(12) United States Patent
Kim

(10) Patent No.: US 6,525,189 B1
(45) Date of Patent: Feb. 25, 2003

(54) MULTIMERIZED DBH ENHANCER DOMAINS

(75) Inventor: Kwang-Soo Kim, Lexington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 09/688,748

(22) Filed: Oct. 16, 2000

Related U.S. Application Data

(60) Provisional application No. 60/159,695, filed on Oct. 15, 1999.

(51) Int. Cl.$^7$ .............................................. C07H 21/04
(52) U.S. Cl. ..................... 536/24.1; 435/69.1; 435/91.1; 435/455
(58) Field of Search ...................... 536/24.1; 435/320.1, 435/69.1, 91.1, 455

(56) References Cited

PUBLICATIONS

Kim et al (1998) Journal of Neuroscience 18:8247–8260.*
Kim et al (1998) Society for Neuroscience Abstracts 24:1265.*
Kim et al (1997) Society for Neuroscience Abstracts 23:352.*
Swanson et al (1997) J. Biol Chem. 272:27382–27392.*
Afar et al.; Positive and negative elements contribute to the cell–specific expression of the rat dopamine beta–hydroxylase gene; Brain Res. Mol. Brain Res.; Feb. 3, 1996; vol. 36, No. 1, pp. 79–92.
Hoyle et al.; Cell–specific expression from the human dopamine beta–hydroxylase promoter in transgenic mice is controlled via a combination of positive and negative regulatory elements; J. Neurosci, May, 1994; vol. 14, 5 pt 1; pp. 2455–2463.
Ishiguro et al.; Identification of a negative regulatory element in the 5'–flanking region of the human dopamine beta–hydroxylase gene; Brain Res. Mol. Brain Res.; Dec. 28, 1995; vol. 34, No. 2, pp. 251–261.
Ishiguro et al.; Neuron–specific expression of the human dopamine beta–hydroxylase gene requires both the cAMP-response element and a silencer region; J. Biol. Chem.; Aug. 25, 1993; vol. 268, No. 24, pp. 17987–17994.

Kim et al.; The cell–specific silencer region of the human dopamine beta–hydroxylase gene contains several negative regulatory elements; J. Neurochem; Jul., 1998; vol. 71, No. 1, pp. 41–50.
Kim et al.; The cAMP–dependent protein kinase regulates transcription of the dopamine beta–hydroxylase gene; J. Neurosci, Nov., 1994; vol. 14, 11 pt 2; pp. 7200–7207.
Kobayashi et al.; Functional and high level expression of human dopamine beta–hydroxylase in transgenic mice; J. Biol Chem.; Nov. 25, 1994; vol. 269, No. 47; pp. 29725–29731.
Morita et al.; The 5'–flanking region of the human dopamine beta–hydroxylase gene promotes neuron subtype–specific gene expression in the central nervous system of transgenic mice; Mol. Brain Res, Mar. 17, 1993; vol.17, No. 3–4; pp. 239–244.
Sabban et al.; Multiple pathways in regulation of dopamine beta–hydroxylase; Adv. Pharmacol, 1998; vol. 42, pp. 53–56.
Seo et al.; Multiple protein factors interact with the cisregulatory elements of the proximal promoter in a cellspecific manner and regulate transcription of the dopamine beta–hydroxylase gene; J. Neurosci; Jul. 1, 1996; vol. 16, No. 13, pp. 4102–4112.
Shaskus, et al.; A negative regulatory element in the rat dopamine beta–hydroxylase gene contributes to the cell type specificity of expression; J. Neurochem; Jan. 1995; vol. 64, No. 1, pp. 52–60.
Yang et al.; Paired–like homeodomain proteins, Phox2a and Phox2b, are responsible for noradrenergic cell–specific transcription of the dopamine β–hydroxylase gene; J. Neurochem; 1998; vol. 71, No. 5, pp. 1813–1826.

* cited by examiner

*Primary Examiner*—James Ketter
*Assistant Examiner*—Bronwen M. Loeb
(74) *Attorney, Agent, or Firm*—Clark & Elbing LLP

(57) ABSTRACT

The invention features an enhancer cassette having the formula $[X-Y]_n$, wherein each X is independently a noradrenergic cell-specific enhancer derived from a DBH gene; Y is absent or is a mono or polynucleotide that has between one and thirty nucleotides; and n is an integer between three and twenty, inclusive.

21 Claims, 12 Drawing Sheets

```
Domain I     -59  GCCTGGACCCCACCCCATTCA  -40           SEQ ID NO: 27
         Im  -59  ............TATG....  -40           SEQ ID NO: 28

Domain II    -87  CCGCTAGACAAATGTGATTACC  -56          SEQ ID NO: 29
         IIm -87  ............GCAGACG...  -56          SEQ ID NO: 30

Domain III   -136 TGAGTGCTTGGCCTGGGGCGCAAGCTTGTGGGAGG  -102   SEQ ID NO: 31
         IIIm -136 ...........................TTA.....  -102   SEQ ID NO: 32
```

```
PRSI      -171 GTGTCATTAGTGCCAATTAGAG -150      SEQ ID NO: 1
                   ****    ****
                   |   |   ||||
Domain II  -87 CCGCTAGACAAATGTGATTACC -56       SEQ ID NO: 2
                   ****
II-m1          ..TA..................           SEQ ID NO: 33
II-m2          .......CTA............           SEQ ID NO: 34
II-m3          ............CT........           SEQ ID NO: 35
II-m4          ..................GC..           SEQ ID NO: 36
```

Domain IIx8-LacZ

NSE-LacZ

1.15DBH-LacZ

SEQUENCE LISTING

```
<160> NUMBER OF SEQ ID NOS: 36

<210> SEQ ID NO 1
<211> LENGTH: 22
<212> TYPE: DNA
<213> ORGANISM: Homo sapiens

<400> SEQUENCE: 1
gtgtcattag tgccaattag ag                                              22

<210> SEQ ID NO 2
<211> LENGTH: 22
<212> TYPE: DNA
<213> ORGANISM: Homo sapiens

<400> SEQUENCE: 2
ccgctagaca aatgtgatta cc                                              22

<210> SEQ ID NO 3
<211> LENGTH: 8
<212> TYPE: DNA
<213> ORGANISM: Homo sapiens
```

```
<400> SEQUENCE: 3 tgacgtcc                                                              8

<210> SEQ ID NO 4
<211> LENGTH: 8
<212> TYPE: DNA
<213> ORGANISM: Homo sapiens

<400> SEQUENCE: 4 tgacgtca                                                              8

<210> SEQ ID NO 5
<211> LENGTH: 6
<212> TYPE: DNA
<213> ORGANISM: Homo sapiens

<400> SEQUENCE: 5 agatcc                                                                6

<210> SEQ ID NO 6
<211> LENGTH: 21
<212> TYPE: DNA
<213> ORGANISM: Homo sapiens

<400> SEQUENCE: 6
gagggaaaat tggattcccc g                                              21

<210> SEQ ID NO 7
<211> LENGTH: 21
<212> TYPE: DNA
<213> ORGANISM: Artificial Sequence
<220> FEATURE:
<223> OTHER INFORMATION: Based on Homo Sapiens

<400> SEQUENCE: 7
gagggaaagc cttcggcccc g                                              21

<210> SEQ ID NO 8
<211> LENGTH: 21
<212> TYPE: DNA
<213> ORGANISM: Artificial Sequence
<220> FEATURE:
<223> OTHER INFORMATION: Based on Homo Sapiens

<400> SEQUENCE: 8
gagggaaaat tggattaccc g                                              21

<210> SEQ ID NO 9
<211> LENGTH: 29
<212> TYPE: DNA
<213> ORGANISM: Homo sapiens

<400> SEQUENCE: 9
gacatgcatg cgcaggctga gtgcttggc                                      29

<210> SEQ ID NO 10
<211> LENGTH: 18
<212> TYPE: DNA
<213> ORGANISM: Homo sapiens

<400> SEQUENCE: 10
cattttagct tccttagc                                                  18
```

```
<210> SEQ ID NO 11
<211> LENGTH: 29
<212> TYPE: DNA
<213> ORGANISM: Homo sapiens

<400> SEQUENCE: 11
gacatgcatg cgctgcctgg acccacccc                                29

<210> SEQ ID NO 12
<211> LENGTH: 18
<212> TYPE: DNA
<213> ORGANISM: Homo sapiens

<400> SEQUENCE: 12
cattttagct tccttagc                                            18

<210> SEQ ID NO 13
<211> LENGTH: 29
<212> TYPE: DNA
<213> ORGANISM: Homo sapiens

<400> SEQUENCE: 13
gacatgcatg cgtccagggc ataaatggc                                29

<210> SEQ ID NO 14
<211> LENGTH: 18
<212> TYPE: DNA
<213> ORGANISM: Homo sapiens

<400> SEQUENCE: 14
cattttagct tccttagc                                            18

<210> SEQ ID NO 15
<211> LENGTH: 26
<212> TYPE: DNA
<213> ORGANISM: Artificial Sequence
<220> FEATURE:
<223> OTHER INFORMATION: Based on Homo Sapiens

<400> SEQUENCE: 15
cctggaccca ctatgttcag gaccag                                   26

<210> SEQ ID NO 16
<211> LENGTH: 26
<212> TYPE: DNA
<213> ORGANISM: Artificial Sequence
<220> FEATURE:
<223> OTHER INFORMATION: Based on Homo Sapiens

<400> SEQUENCE: 16
cctggtcctg aacatagtgg gtccag                                   26

<210> SEQ ID NO 17
<211> LENGTH: 29
<212> TYPE: DNA
<213> ORGANISM: Artificial Sequence
<220> FEATURE:
<223> OTHER INFORMATION: Based on Homo Sapiens

<400> SEQUENCE: 17
ccgctagaca agcagacgta cccgtgctg                                29

<210> SEQ ID NO 18
<211> LENGTH: 29
<212> TYPE: DNA
```

```
<213> ORGANISM: Artificial Sequence
<220> FEATURE:
<223> OTHER INFORMATION: Based on Homo Sapiens

<400> SEQUENCE: 18
gcagcacggg tacgtctgct tgtctagcg                                      29

<210> SEQ ID NO 19
<211> LENGTH: 35
<212> TYPE: DNA
<213> ORGANISM: Artificial Sequence
<220> FEATURE:
<223> OTHER INFORMATION: Based on Homo Sapiens

<400> SEQUENCE: 19
tgagtgcttg gcctggttag caagcttgtg ggagg                               35

<210> SEQ ID NO 20
<211> LENGTH: 35
<212> TYPE: DNA
<213> ORGANISM: Artificial Sequence
<220> FEATURE:
<223> OTHER INFORMATION: Based on Homo Sapiens

<400> SEQUENCE: 20
ccctcccaca agcttgctaa ccaggccaag cactc                               35

<210> SEQ ID NO 21
<211> LENGTH: 24
<212> TYPE: DNA
<213> ORGANISM: Artificial Sequence
<220> FEATURE:
<223> OTHER INFORMATION: Based on Homo Sapiens

<400> SEQUENCE: 21
ccatgtgtca ccggtgccaa ttag                                           24

<210> SEQ ID NO 22
<211> LENGTH: 24
<212> TYPE: DNA
<213> ORGANISM: Artificial Sequence
<220> FEATURE:
<223> OTHER INFORMATION: Based on Homo Sapiens

<400> SEQUENCE: 22
ctaattggca ccggtgacac atgg                                           24

<210> SEQ ID NO 23
<211> LENGTH: 24
<212> TYPE: DNA
<213> ORGANISM: Artificial Sequence
<220> FEATURE:
<223> OTHER INFORMATION: Based on Homo Sapiens

<400> SEQUENCE: 23
cattagtgcc aaccggagga gggc                                           24

<210> SEQ ID NO 24
<211> LENGTH: 24
<212> TYPE: DNA
<213> ORGANISM: Artificial Sequence
<220> FEATURE:
<223> OTHER INFORMATION: Based on Homo Sapiens

<400> SEQUENCE: 24
gccctcctcc ggttggcact aatg                                           24
```

```
<210> SEQ ID NO 25
<211> LENGTH: 26
<212> TYPE: DNA
<213> ORGANISM: Artificial Sequence
<220> FEATURE:
<223> OTHER INFORMATION: Based on Homo Sapiens

<400> SEQUENCE: 25
caccggtgcc aaccggagga gggcag                                    26

<210> SEQ ID NO 26
<211> LENGTH: 26
<212> TYPE: DNA
<213> ORGANISM: Artificial Sequence
<220> FEATURE:
<223> OTHER INFORMATION: Based on Homo Sapiens

<400> SEQUENCE: 26
gctgccctcc tccggttggc accggt                                    26

<210> SEQ ID NO 27
<211> LENGTH: 20
<212> TYPE: DNA
<213> ORGANISM: Homo sapiens

<400> SEQUENCE: 27
gcctggaccc accccattca                                           20

<210> SEQ ID NO 28
<211> LENGTH: 20
<212> TYPE: DNA
<213> ORGANISM: Artificial Sequence
<220> FEATURE:
<223> OTHER INFORMATION: Based on Homo Sapiens

<400> SEQUENCE: 28
gcctggaccc actatgttca                                           20

<210> SEQ ID NO 29
<211> LENGTH: 22
<212> TYPE: DNA
<213> ORGANISM: Homo sapiens

<400> SEQUENCE: 29
ccgctagaca aatgtgatta cc                                        22

<210> SEQ ID NO 30
<211> LENGTH: 22
<212> TYPE: DNA
<213> ORGANISM: Artificial Sequence
<220> FEATURE:
<223> OTHER INFORMATION: Based on Homo Sapiens

<400> SEQUENCE: 30
ccgctagaca agcagacgta cc                                        22

<210> SEQ ID NO 31
<211> LENGTH: 35
<212> TYPE: DNA
<213> ORGANISM: Homo sapiens

<400> SEQUENCE: 31
tgagtgcttg gcctggggcg caagcttgtg ggagg                          35
```

<210> SEQ ID NO 32
<211> LENGTH: 35
<212> TYPE: DNA
<213> ORGANISM: Artificial Sequence
<220> FEATURE:
<223> OTHER INFORMATION: Based on Homo Sapiens

<400> SEQUENCE: 32
tgagtgcttg gcctggttag caagcttgtg ggagg          35

<210> SEQ ID NO 33
<211> LENGTH: 22
<212> TYPE: DNA
<213> ORGANISM: Artificial Sequence
<220> FEATURE:
<223> OTHER INFORMATION: Based on Homo Sapiens

<400> SEQUENCE: 33
cctatagaca aatgtgatta cc          22

<210> SEQ ID NO 34
<211> LENGTH: 22
<212> TYPE: DNA
<213> ORGANISM: Artificial Sequence
<220> FEATURE:
<223> OTHER INFORMATION: Based on Homo Sapiens

<400> SEQUENCE: 34
ccgctagcta aatgtgatta cc          22

<210> SEQ ID NO 35
<211> LENGTH: 22
<212> TYPE: DNA
<213> ORGANISM: Artificial Sequence
<220> FEATURE:
<223> OTHER INFORMATION: Based on Homo Sapiens

<400> SEQUENCE: 35
ccgctagaca aacttgatta cc          22

<210> SEQ ID NO 36
<211> LENGTH: 22
<212> TYPE: DNA
<213> ORGANISM: Artificial Sequence
<220> FEATURE:
<223> OTHER INFORMATION: Based on Homo Sapiens

<400> SEQUENCE: 36
ccgctagaca aatgtgatgc cc          22

US 6,525,189 B1

MULTIMERIZED DBH ENHANCER DOMAINS

This application claims benefit from U.S. provisional patent application No. 60/159,695, filed Oct. 15, 1999, hereby incorporated by reference.

STATEMENT AS TO FEDERALLY SPONSORED RESEARCH

This invention was sponsored in part by Grant #RO1-MH48866 from the National Institutes of Health. The Government has certain rights to this invention. This application claims priority from U.S. provisional patent application No. 60/159,695, filed Oct. 15, 1999.

BACKGROUND OF THE INVENTION

The invention relates to the field of cell type-specific gene expression.

Dopamine β-hydroxylase (DBH) is a hallmark protein of noradrenergic neurons because noradrenaline is synthesized by this enzyme. The highly restricted pattern of DBH expression in the nervous system predicts that this gene is subject to neuron-specific as well as to cell type-specific control mechanisms. Transgenic mice experiments have shown that 5.8 or 4 kb of the 5' flanking sequences of the human DBH gene can drive expression of the reporter gene in neurons of the locus coeruleus as well as other noradrenergic neurons and adrenal chromaffin cells, albeit with some ectopic expression. More recently, comparison of reporter gene expression in transgenic animals generated by using DBH 5' flanking regions of different lengths indicated that the upstream region between −1.1 and −0.6 kb is necessary for expression in adult and fetal noradrenergic Neurons. Using cell culture systems, we and others have demonstrated that the 5' upstream region of the DBH gene can drive reporter gene expression in a cell-specific manner.

Deletional and site-directed mutational analyses have indicated that as little as 486 bp of the upstream sequence of the human DBH gene can direct expression of a reporter gene in a cell type-specific manner. In the 486 bp region of the human DBH gene, the distal part spanning −486 to −263 bp appears to have a cell-specific silencer function which contributed to suppression of the promoter activity in non-neuronal cells. Transient transfection assays identified the proximal part spanning −262 to +1 bp as sufficient and essential for the high-level DBH promoter activity in DBH-positive cells. In this 262 bp proximal area, four protein-binding regions (domains I to IV) have been identified by DNase I footprinting analysis. A cAMP response element (CRE), 5'-TGACGTCC-3' (SEQ ID NO: 3), with a single base deviation from the consensus octamer motif, 5'-TGACGTCA-3' (SEQ ID NO: 4), was shown to be critical for both the basal and cAMP-inducible transcription in DBH-expressing cell lines. This CRE is included in a composite enhancer domain structure located at −185 to −150 bp, designated domain IV, which contains several additional cis-elements such as AP1, YY 1, and two core motifs of homeodomain (HD) binding sites. Site-directed mutagenesis of each sequence motif has revealed that the CRE is essential for basal promoter activity in every cell line, YY1 is multifunctional, and the AP1-like motif may be transcriptionally inactive.

The murine paired-like HD protein, Phox2a, is selectively expressed in noradrenergic cells and is critical for development of several noradrenergic neuron populations, including the locus coeruleus. The forced expression of Phox2a robustly activates DBH promoter activity, strongly suggesting a mechanism for noradrenergic-specific promoter function. Moreover, Phox2b, which contains an HD identical to that of Phox2a, has been identified and shown to be widely coexpressed with Phox2a in both the central and peripheral nervous system. Cotransfection assays showed that Phox2a and Phox2b transactivate the DBH promoter activity with a comparable efficiency.

SUMMARY OF THE INVENTION

We have discovered that an expression construct that included multiple copies of noradrenergic-specific enhancer domains isolated from the DBH gene increased the minimal promoter activity by 100- to 200-fold in DBH-positive cell lines. Moreover, we discovered that this expression construct maintained the cell-type specificity exhibited by the natural DBH promoter.

Accordingly, the invention features an enhancer cassette having the formula $[X-Y]_n$, wherein each X is independently a noradrenergic cell-specific enhancer derived from a DBH gene; Y is absent or is a mono or polynucleotide that has between one and thirty nucleotides; and n is an integer between three and fifty, inclusive. Preferably, the noradrenergic cell-specific enhancer binds specifically to Phox 2a, Phox2b, or both. Also preferably, X is independently selected from the group consisting of 5'-GTGTCATTAGTGCCAATTAGAG-3' (SEQ ID NO: 1) and 5'-CCGCTAGACAAATGTGATTACC-3' (SEQ ID NO: 2); Y is absent or is a mono or polynucleotide that has between one and six nucleotides; and n is between three and twenty, inclusive. In other embodiments, X includes a region that shares greater than 70% sequence identity with SEQ ID NO: 1 or SEQ ID NO: 2 and binds to Phox2a or Phox2b.

The enhancer cassette is useful for expressing a nucleic acid molecule in a noradrenergic cell. To this end, the enhancer cassette can be combined with an RNA polymerase binding site and a transcription initiation site to form an expression construct. Additionally, the enhancer cassette and expression construct of the invention can each be a component of an expression vector, such as an adenoviral vector.

As used herein, by "nucleic acid" is meant either DNA or RNA. A "nucleic acid molecule" may be a single-stranded or double-stranded polymer of deoxyribonucleotide or ribonucleotide bases. Unless otherwise specified, the left hand direction of the sequence of a single-stranded nucleic acid molecule is the 5' end, and the left hand direction of double-stranded nucleic molecule is referred to as the 5' direction.

By "promoter" is meant a region of nucleic acid, upstream from a translational start codon, which is involved in recognition and binding of RNA polymerase and other proteins to initiate transcription. A "DBH promoter" is one derived from the promoter region of a DBH gene and that, when operably linked to a heterologous nucleic acid molecule, is capable of initiating transcription of that molecule when present in a transcription medium capable of supporting transcription.

Exemplary transcription media include, for example, a mammalian cell (e.g., an immortalized cell), and a yeast cell. Also included are in vitro expression systems such as reconstituted expression medium composed of components required to support transcription, as are known in the art.

By "enhancer domain" or "domain" is meant a nucleic acid sequence that, when positioned proximate to a promoter and present in a transcription medium capable of supporting transcription, confers increased transcription activity relative to the transcription activity resulting from the promoter in the absence of the enhancer domain. By "enhancer cassette" is meant a nucleic acid sequence that includes an enhancer domain and, optionally, additional sequence that does not enhance transcription (e.g., spacer sequence).

By "multimerized enhancer domain" is meant two or more copies of a noradrenergic cell-specific enhancer domain derived from a DBH gene. Preferably, the number of copies is between three and twenty, inclusive. The enhancer domains can be in the same or opposite orientation, and can be contiguous or noncontiguous. In expression constructs having two different enhancer domains (e.g., domain A and domain B), the orientation and the 5' to 3' order (e.g., 5'-AABB-3' vs. 5'-ABAB-3') are not limitations to the invention.

By "operably linked" is meant that a nucleic acid molecule to be transcribed and an expression construct (i.e., a promoter and an enhancer domain) are connected in such a way as to permit transcription of the nucleic acid molecule in a suitable transcription medium.

By "derived from" is meant that a the nucleic acid molecule was either made or designed from a second nucleic acid molecule, the derivative retaining important functional features of the nucleic acid molecule from which it was made or designed. In the case of enhancer domains, the important features are specific binding to Phox2a and/or Phox2b and conferral of noradrenergic cell-specific expression when operably linked to a promoter. Optimization of binding and/or cell-specific expression may be performed.

By "expression construct" is meant a nucleic acid molecule that is capable of directing transcription. An expression construct of the present invention includes, at the least, a multimerized DBH enhancer domain and a promoter. Additional domains, such as a transcription termination signal, may also be included, as described herein.

By "vector" or "expression vector" is meant an expression system (e.g., an adenoviral expression system), a nucleic acid-based shuttle vehicle, a nucleic acid molecule adapted for nucleic acid delivery, or an autonomous self-replicating circular DNA (e.g., a plasmid). When a vector is maintained in a host cell, the vector can either be stably replicated by the cells during mitosis as an autonomous structure, incorporated within the genome of the host cell, or maintained in the host cell's nucleus or cytoplasm.

By "plasmid" is meant an autonomous DNA molecule capable of replication in a cell, and includes both expression and nonexpression types.

By "heterologous" is meant that the nucleic acid molecule originates from a foreign source or, if from the same source, is modified from its original form. Thus, a "heterologous promoter" is a promoter not normally associated with the multimerized enhancer domain of the present invention. Similarly, a heterologous nucleic acid molecule that is modified from its original form or is from a source different from the source from which the promoter to which it is operably linked was derived.

By "transgene" is meant any piece of a nucleic acid molecule (for example, DNA) which is inserted by artifice into a cell, and becomes part of the organism (integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

Other features and advantages of the invention will be apparent from the following description of the preferred embodiments thereof.

DETAILED DESCRIPTION OF THE INVENTION

Figures 1A, 1B:
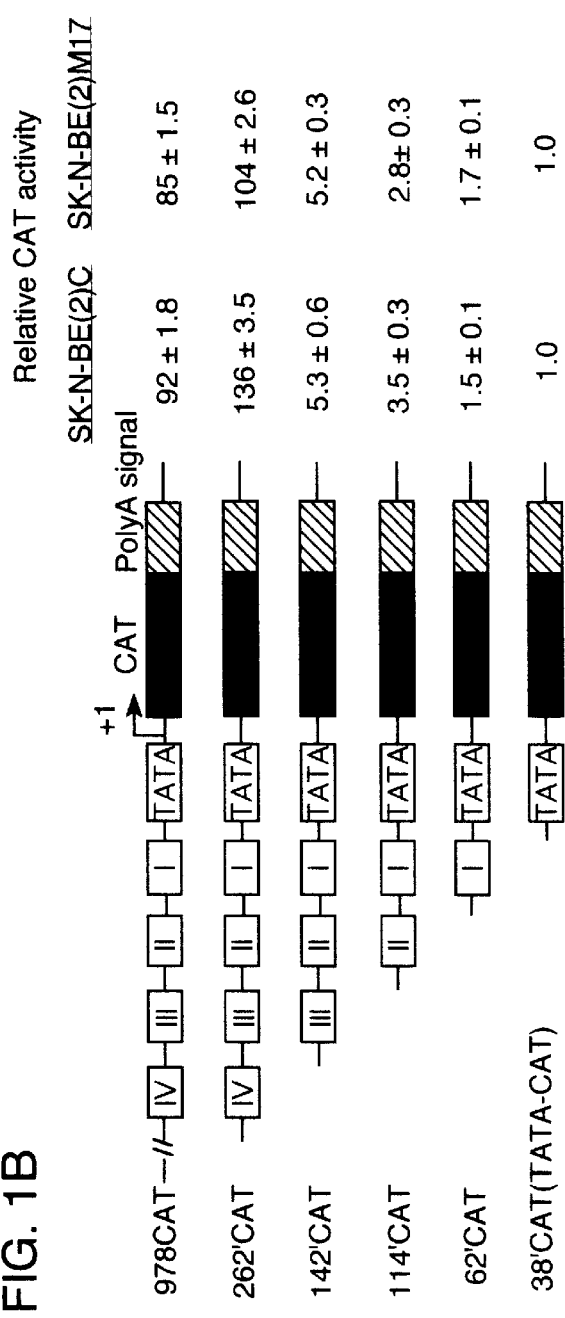
FIG. 1A is a schematic illustration showing the nucleotide sequences and he locations of domains I, II, and III of the human DBH gene, as identified by DNase I footprint analysis. The Sp1-binding motif and AP2-binding motif residing in domain I and III, respectively, are indicated by brackets. Base substitutions within each domain which are analyzed by EMSA and transient transfection assays are also indicated.
FIG. 1B is a schematic illustration showing the promoter activity of deletional DBH-CAT reporter constructs, as determined by transient transfection assays in DBH-expressing SK-N-BE(2)C and SK-N-BE(2)M17 cell lines, and expressed relative to that of the minimal 38' CAT construct.

We have discovered that Phox2a interacts with the HD binding site residing within domains II and IV of the human DBH gene in a cell-specific manner and can directly control noradrenergic cell-specific DBH promoter activity. Multimerization of domain II increased the promoter activity of a minimal DBH promoter by approximately 2000-fold in DBH-positive cell lines without compromising cell specificity. Cotransfection of a Phox2a-expression vector dramatically increased the activity of the multiple domain II-promoter construct only in DBH-negative cell lines, confirming that domain II is responsive to Phox2a.

In vivo, an adenoviral expression vector containing the multimerized DBH enhancer domains exhibited strong expression and greater cell-specific expression than did the entire 1.1 kb DBH promoter, indicating that the duplicated enhancer domains will be useful, for example, for driving robust gene expression in noradrenergic cells in gene therapy.

We have also discovered a Phox2a binding site that can be mutated to increase expression levels in noradrenergic cells.

Multimerized DBH Enhancer Domains

In one embodiment, the invention features multimerized enhancer domains. The multimerized enhancer domains of the invention are derived from DBH genomic sequence. Taking the first nucleotide of the mRNA as position +1, noradrenergic enhancer domains are located, for example, from about −150 to −171 and −66 to −87. It will be understood that the nucleotide positions can be altered by about five to ten base pairs without substantially altering the transcription-enhancing ability of an enhancer domain. The enhancer domain that is multimerized will usually be about 10 to 40 bp in length. In addition to the noradrenergic cell-specific enhancer domains described herein, the invention features enhancer domains that are variants or modifications of these enhancer domains. For example, one or more nucleotides of the enhancer domain can be altered, using standard techniques, without altering Phox2a-specific binding or noradrenergic cell-specific expression. Using techniques described herein, one can readily ascertain whether any alteration of an enhancer domain results in either altered binding or expression.

We have now discovered that the property that results in noradrenergic cell-specific expression is most likely to be binding to Phox2a and/or Phox2b. Moreover, these two transcription factors bind to both domain II and domain IV, even though the two domains share little sequence identity. Based on our findings, we can generate, using standard techniques such as PCR or oligonucleotide synthesis, artificial enhancer domains that specifically bind to Phox2a and/or Phox2b and increase promoter activity specifically in noradrenergic cells. Thus, any multimerized enhancer domain that specifically binds Phox2a and/or Phox2b is considered part of the invention.

Preferably, the multimerized enhancer domain is incorporated into an enhancer cassette having the formula $(X-Y)_n$, wherein X corresponds to a noradrenergic cell-specific enhancer derived from a DBH gene, Y is absent or is a mono or polynucleotide that has between one and thirty nucleotides, and n is an integer between 3 and 50 inclusive (preferably between 8 and 16). It is understood that n can be even greater than 50 (e.g., 100, 200, 500, or more). In preferred embodiments, X has a sequence selected from a group consisting of 5'-GTGTCATTAGTGCCAATTAGAG-3' (SEQ ID NO: 1) and 5'-CCGCTAGACAAATGTGATTACC-3' (SEQ ID NO: 2). In other embodiments, X has greater than 70% sequence identity to SEQ ID NO: 1 or SEQ ID NO: 2 and binds to Phox 2a or Phox 2b.

Although domain IV contains several cis-elements critical for DBH transcription, when placed 5' to the TATA and transcription start site, it was able to recapitulate neither intact basal level nor noradrenergic cell-specific transcription of the reporter gene. This lack of specificity is most likely due to the inclusion of the CRE, which is not cell-specific, and thus it is preferred that multimerized enhancer domains do not include CREs. Multimerized enhancer domains results in greatly increased promoter activity; either domain II or domain IV alone mediated Phox2a/Phox2b-induced transcription only modestly (approximately 3-fold) compared to the intact DBH promoter-enhancer region (10- to 15-fold).

Expression Constructs

In one particular embodiment of the present invention, the multimerized enhancer domains or enhancer cassettes are placed in the proximity of a promoter; together, these form an expression construct. An exemplary expression construct is shown in FIG. 6.

An enhancer domain is cis-acting and desirably is located within about 5 kb, typically about 2 kb, more typically adjacent to or within about 1 kb of a promoter to be enhanced. The combination of the multimerized enhancer domain and the promoter is considered to be an "expression construct." In the expression construct, the enhancer domains may be in either orientation with respect to each other as well as to the promoter, and can be located 5' or 3' in relation to the promoter they enhance, usually in the 5' direction.

A multimerized enhancer domain finds use with a wide variety of promoters, including promoters that are naturally found under the control of the enhancer, i.e., in a cis position (adjacent and homologous) and those not normally associated with the particular promoter (i.e., heterologous).

The promoter may be derived from the same or different kingdom, family, or species as the multimerized DBH enhancer domains. Sources of promoters include viruses, prokaryotes and eukaryotes, such as bacteria, plants, insects, and mammals.

In addition to the aforementioned multimerized enhancer domain and promoter, the expression constructs may also include regulatory control regions which are generally present in the 3' regions of human genes. For example, a 3' terminator region may be included in the expression vector to increase stability of the mRNA.

Expression Vectors

In addition to an expression construct, an expression vector typically contains a dominant selectable marker gene used to identify those cells that have become transformed. Useful selectable genes include genes encoding antibiotic resistance genes, for example, those encoding resistance to hygromycin, kanamycin, bleomycin, G418, streptomycin, or spectinomycin. Alternatively, the green-fluorescent protein from the jellyfish *Aequorea victoria* may be used as a selectable marker.

The invention also contemplates DNA constructs in which an expression construct, including a multimerized noradrenergic cell-specific enhancer domain and a promoter, is operably linked to a nucleic acid molecule one wishes to be transcribed. The nucleic acid molecule may have a natural open reading frame (ORF), as well as transcribed 5' and 3' sequences flanking the ORF. Alternatively, it may be in the "antisense" orientation in that it encodes the complement of an RNA molecule or portion thereof. When the construct includes an ORF (which encodes a polypeptide), an enhanced transcription initiation rate is obtained, usually providing an increased amount of the polypeptide. For protein production, translational initiation sequences (including a start codon) are included in the constructs, either from the promoter domain, from the attached coding sequences, or from a heterologous source. When the construct contains an antisense sequence, complementary to the wild-type molecule, decreases the amount of polypeptide product. The nucleic acid molecules of interest which are transcribed will be of at least about 8 bp, usually at least about 12 bp, more usually at least about 20 bp, and may be one kb or more in length.

Methods for Making Multimerized Enhancer Domains

A variety of multimerized DBH enhancer domains can be produced using standard molecular biology techniques. For example, a multimerized enhancer can be constructed by first mapping restriction enzyme sites in the DBH genomic sequence that includes the enhancer domain of interest, then, using the constructed map to determine the appropriate restriction enzymes, excising the domain of interest and recombining it to form a multimerized enhancer domain. Alternatively, a multimerized enhancer domain or an expression construct of the present invention can be synthesized by a variety of methods based on the sequences described herein. Synthesis can be accomplished by chemical synthesis methods for the production of enhancer oligonucleotides. In addition, a nucleic acid molecule can be prepared by the synthesis of a series of oligonucleotides which correspond to different portions of the nucleic acid molecule, and which can be combined by ligation to form larger nucleic acid molecules. Finally, oligonucleotides can be used as primers in a polymerase chain reaction (PCR) to amplify a nucleic acid molecule of interest. The primers can further contain restriction sites to facilitate ligation of the PCR fragments.

The expression constructs are typically prepared employing cloning vectors, where the sequences may be naturally occurring, mutated sequences, synthetic sequences, or combinations thereof. The cloning vectors are well known and include prokaryotic or eukaryotic replication systems, markers for selection of transformed host cells, and unique dual restriction sites for insertion or substitution of sequences.

EXAMPLE 1

Phox2a is Coexpressed with DBH and Interacts with the Putative HD-binding Site of the Human DBH Gene in a Cell-specific Manner Domain IV, located at −185 to −150 bp upstream of the transcription start site of the human DBH gene, contains several potential cis-regulatory elements such as the CRE, AP1, YY1, and two core motifs of HD-binding site in an overlapping composite structure. Previous studies have indicated that this region is critical for DBH transcription, and multiple protein factors may bind to this region in a cell-specific manner. To identify noradrenergic-specific DNA-protein complexes, nuclear extracts from DBH-expressing (SK-N-BE(2)C, CATH.a, and PC12) and nonexpressing (HeLa and C6 glioma) cell lines were compared by EMSA. Using radiolabeled oligonucleotide C/Y/A and domain IV as the probe, we failed to identify any DNA-protein complex which, either directly or indirectly, correlated with the noradrenergic phenotype. To determine whether any cognate protein factors interact with the HD-binding site in a noradrenergic-specific pattern, we incubated different nuclear extracts with radiolabeled oligonucleotide HD and analyzed DNA-protein complexes in EMSA. Two major complexes were formed by most nuclear extracts. Thus, both DBH-expressing and -nonexpressing cell lines appear to contain a protein factor that bound to the HD site of the DBH gene. Nuclear extracts from C6 glioma cells produced several complexes with faster mobility. The DNA-protein complexes, including those formed by C6 extracts, were competed by an excess of HD oligonucleotide, but not by other nonrelated oligonucleotides (e.g., Sp1), indicating that they represent sequence-specific complexes. To determine whether the two ATTA core motifs, designated HD1 and HD2, are important for forming these complexes, we performed competition assays using wild type or mutant oligonucleotides. HDm1, containing substitutions within HD1, competed formation of DNA-protein complexes as efficiently as did wild type HD oligonucleotide. In contrast, HDm2 was unable to compete formation of complexes, indicating that HD2, but not HD1, is critical for formation of these complexes in all these cell lines. Consistent with this, radiolabeled HDm1 produced DNA-protein complexes as robustly as the wild type, but radiolabeled HDm2 barely formed any complex.

We next tested whether Phox2a is involved in forming complexes with the HD-binding site. Supershifted bands were specifically formed with the radiolabeled wild type HD oligonucleotide when Phox2a-specific antibody (raised against the carboxy terminus of Phox2a; described in Tiveron et al., J. Neurosci. 16:7649–7660, 1996) was preincubated with nuclear extracts from DBH-expressing cell lines but not with those from DBH-negative cell lines. When nuclear extracts were preincubated with preimmune serum or antibodies against CREB or Sp1, no supershifted bands were detected. This result indicates that Phox2a is restrictively expressed in DBH-expressing cell lines, although other HD-binding proteins evidently also exist in all cell lines. The overall level of DNA-protein complex formation was not noticeably diminished even though supershifted bands were conspicuously formed. While this finding suggests that Phox2a may constitute only a small portion of protein factors that interact with the HD site, it also indicates that properties of Phox2a protein, e.g., stability or DNA-binding affinity, can be modulated by interaction with specific antibody. Using two additional Phox2a-specific antibodies that were raised against Y75-R88 of Phox2a, identical results were obtained in supershift assays.

We examined the correlated expression of DBH and Phox2a in greater detail using mRNAs prepared from five catecholaminergic (human neuroblastoma SK-N-BE(2)C and SK-N-BE(2)M17, rat pheochromocytoma PC12, and mouse CATH.a and PATH.2) and five noncatecholaminergic (human HeLa, human cholinergic neuroblastoma SK-N-MC11, rat glioma C6, human thyroid carcinoma, and mouse mastocytoma) cell lines. We found a striking correlation of DBH and Phox2a expression among all these cell lines analyzed. All three DBH-expressing cell lines appeared to produce a major Phox2a transcript of 1.7 kb, as previously reported (Valarche et al., Development, 119: 881–896, 1993). Additional Northern blot experiments with longer run of samples indicated that the human SK-N-BE(2)C and SK-N-BE(2)M17 cell lines produce a slightly bigger (2.0 kb) transcript of Phox2a, compared to the rat PC12 and mouse CATH.a and PATH.2 cell lines (1.7 kb). Interestingly, Phox2b transcript was expressed in only SK-N-BE(2)C and PC12 cell lines. All five non-catecholaminergic cell lines did not express any detectable message RNA for TH, DBH, Phox2a, or Phox2b.

EXAMPLE 2

Mutation of a Single HD Core Motif Converts the Upstream Region of the DBH Gene into a Nonspecific Enhancer To determine the role of individual cis-regulatory elements residing within domain IV in cell-specific DBH transcription, we mutagenized individual motifs in the context of the 978 bp upstream sequence of the human DBH gene, which is able to direct cell-specific transcription in the transient expression assay (Ishiguro et al., J. Biol. Chem., 268:17987–17994, 1993). Base substitutions within the CRE motif diminished most DBH promoter activity in DBH-expressing and -nonexpressing cell lines alike. This result indicates that the CRE is important for DBH promoter function regardless of the cell type. Mutation of three bases within HD2, which blocked DNA-protein interaction at the HD-binding region in EMSA, virtually abolished transcriptional activity in SK-N-BE(2)C cell line and significantly diminished transcriptional activity (60–80%) in SK-N-BE(2)M17 and CATH.a cell lines. Strikingly, the same mutation did not alter or modestly increased the transcriptional activity in DBH-negative HeLa and C6 cells. Thus, HD2 appears to be exclusively active in noradrenergic cell lines. Another HD-binding core motif, HD1, was also mutated to make themHD 1 construct. This mutation likewise diminished, albeit to a lesser degree, the transcriptional activity in all three DBH-expressing cell lines but did not alter transcriptional activity in DBH-nonexpressing cell lines. The prominent effect of HD1 mutation on DBH promoter function was rather surprising in view of EMSA results, which indicated that this mutation barely affects DNA-protein interaction at this region. Simultaneous mutation of HD1 and HD2 diminished the DBH promoter activity in SK-N-BE(2)M17 and CATH.a cells more severely. Mutation analysis did not support the YY1 and AP1-like motif as noradrenergic-specific enhancers.

EXAMPLE 3

Expression of Phox2a or Phox2b in DBH-nonexpressing Cells Transactivates the Promoter Activity of the Human DBH Gene The observations that the HD-binding site of domain IV is a critical cell-specific enhancer and that its cognate factors Phox2a and Phox2b are expressed only in DBH-positive cells led us to hypothesize that they play a direct role in cell-specific transcription of the DBH gene. To test this, Phox2a- and Phox2b-expressing vectors were transiently cotransfected along with the DBH-CAT reporter gene construct. Transcriptional activity of DBH978CAT was not significantly modulated by Phox2a or Phox2b in SK-N-BE(2)C cells. In contrast, expression of either Phox2a or Phox2b activated the transcriptional activity of DBH978CAT up to 10-fold in a dose-responsive manner in C6 cells. Coexpression of Phox2a and Phox2b marginally potentiated their transactivating function, indicating that they are functionally independent. We further tested the transactivating function of Phox2a and Phox2b in additional DBH-expressing and nonexpressing cell lines. In the CATH.a cells, expression of Phox2a and/or Phox2b modestly facilitated the transcriptional activity of DBH978CAT. In HeLa cells, expression of Phox2a and/or Phox2b activated the transcriptional activity of DBH978CAT up to 15-fold.

EXAMPLE 4

Transcription of the Human DBH gene requires Synergy of Four Proximal Protein-binding Sites In transient transfection assays using DBH-expressing SK-N-BE(2)C and SK-N-BE(2)M17 cell lines (FIG. 1B), deletion of domain IV resulted in a dramatic decrease (20- to 30-fold) of the transcription activity in both cell lines. Further deletion of domains III, II, and I resulted in a progressive decrease of the promoter activity, indicating that all three domains may act as positive regulators of the DBH promoter function in DBH-positive cells.

Figure 1C:
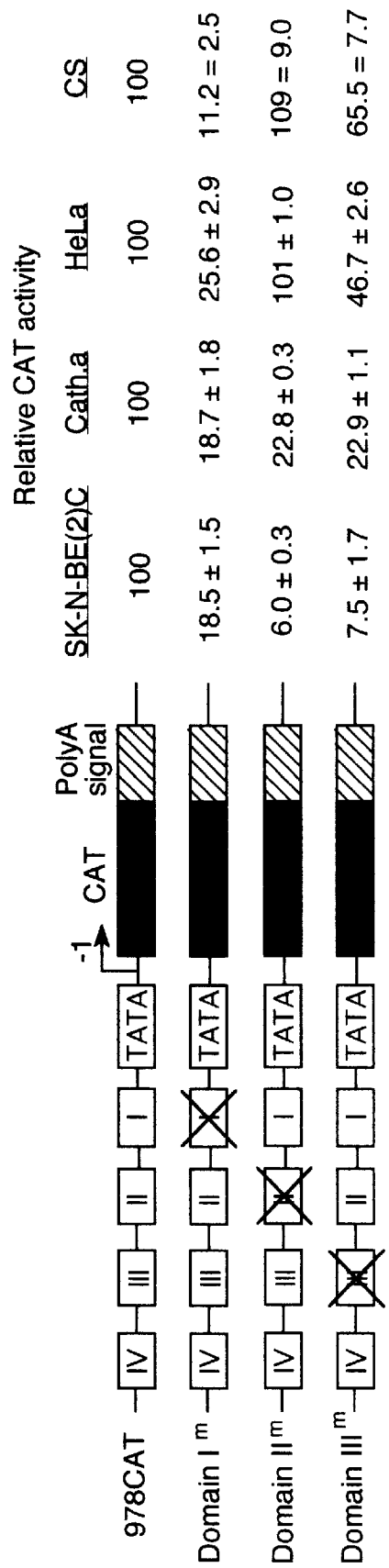
FIG. 1C is a schematic illustration showing the effect of site-directed mutation of each cis-regulatory element on DBH promoter activity in the context of the upstream 978 bp sequences in DBH-expressing (SK-N-BE(2)C and CATH.a) and nonexpressing (HeLa and C6) cell lines. The normalized CAT activity driven by 978CAT in each cell line was set to 100 to compare the effect of each mutation on cell-specific promoter function of the DBH upstream sequence. The relative values are presented as mean ±SEM values from six to eight independent samples.

Base substitutions within each motif were introduced in the context of the 978 bp DBH promoter-enhancer region and examined for effects on promoter activity in both DBH-positive and -negative cells (FIG. 1C). The CAT activity driven by the intact 978 bp DBH promoter-enhancer in DBH-positive cell lines was much higher than that in DBH-negative cell lines (typically >10-fold), but was given the relative value of 100 in each cell line to compare the relative effect of individual mutation on the promoter activity. Base substitutions within domain I, II, or III diminished greater than 80% of the promoter activity in DBH-positive cells, suggesting that these proximal cis-elements activate DBH transcription in an interdependent manner. Mutation of domain I equally diminished most of DBH promoter activity in DBH-negative cell lines, while domain III mutation was several-fold less effective in the negative cell lines. Base substitutions in domain II diminished DBH promoter activity only in DBH-expressing cells, indicating that domain II is a critical noradrenergic cell-specific cis-acting element.

Figure 2:
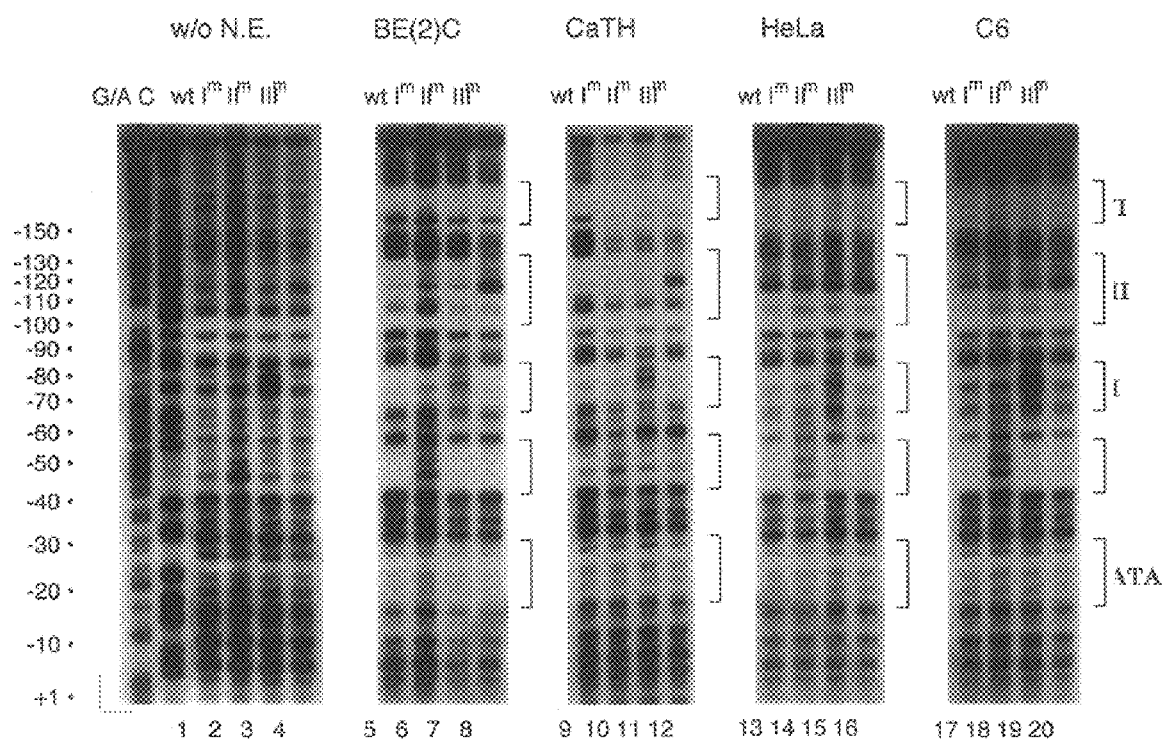
FIG. 2 is a series of photographs of autoradiographs showing nuclear extracts from SK-N-BE(2)C, CATH.a, HeLa, and C6 cells used for DNase I footprinting analyses of the wild type and mutant sequence upstream from the human DBH gene. The coding strand probes were prepared using wild type (lane 1), domain Im (lane 2), domain IIm (lane 3), and domain IIIm (lane 4) mutant constructs. The TATA box and four footprinted domains are denoted by brackets at the right side of the panel.

Using different nuclear extracts, we next performed DNase I footprint analyses of the wild type and mutant promoter-enhancers (FIG. 2) to address (i) whether there is a positive correlation between promoter function and DNA-protein interaction and (ii) whether cognate nuclear factors synergistically bind to these proximal protein binding sites. We found that patterns of DNA-protein interaction appeared to be significantly different between DBH-positive and -negative cell lines. For example, a hypersensitive site at −161 bp appeared only with DBH-positive extracts. Moreover, footprinting at domains II and III was much more evident with DBH-positive extracts (FIG. 2; compare lanes 5 and 9 with 13 and 17). Mutation of each motif specifically blocked footprinting at that site, demonstrating a direct correlation between promoter function and DNA-protein interaction at each motif. Mutation of one site did not impair DNA-protein interactions at other sites, including domain IV, suggesting that the transcription factors bind to the corresponding sites independently of each other. This conclusion was further supported by additional footprinting experiments using suboptimal amounts of nuclear extracts, which protected these domains only incompletely.

EXAMPLE 5

Domain II Interacts with Cognate Protein Factors in a Cell-specific Manner

Figure 3A:
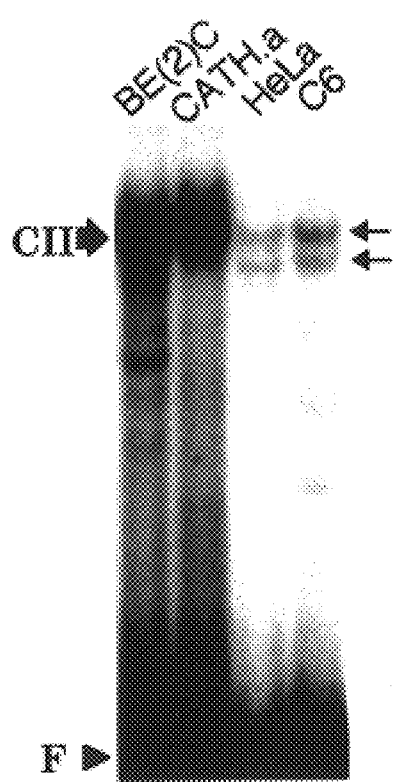
FIGS. 3A and 3B are a series of photographs of autogradiographs showing that domain II interacts with nuclear proteins in a cell-specific manner.
Figure 3B:
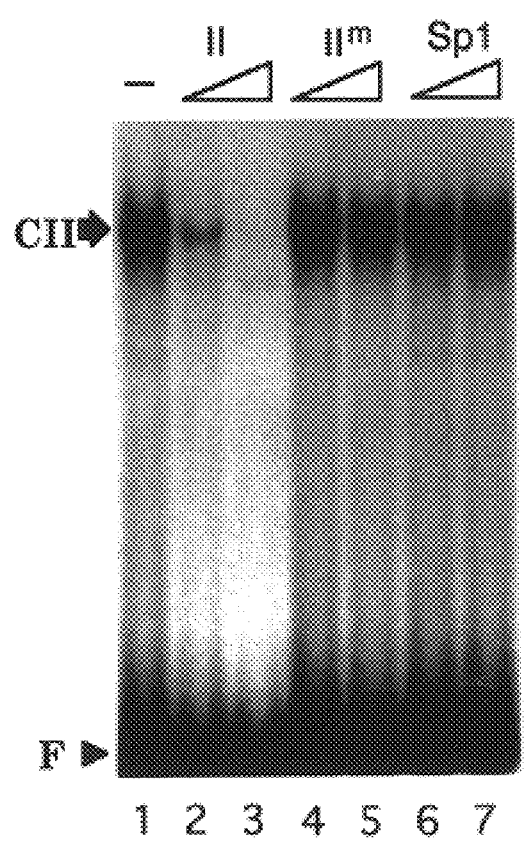
Figure 4A:
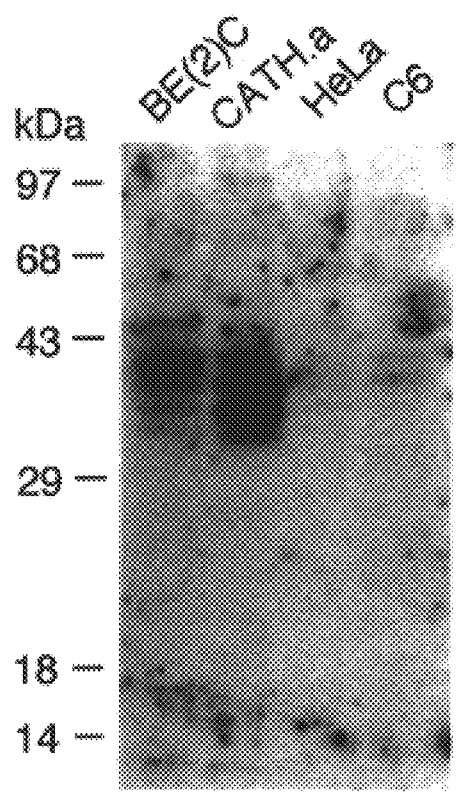
FIGS. 4A and 4B are photographs of autoradiographs showing the identification of noradrenergic neuron-specific protein factors that interact with domain II by Southwestern blot analysis.
Figure 4B:
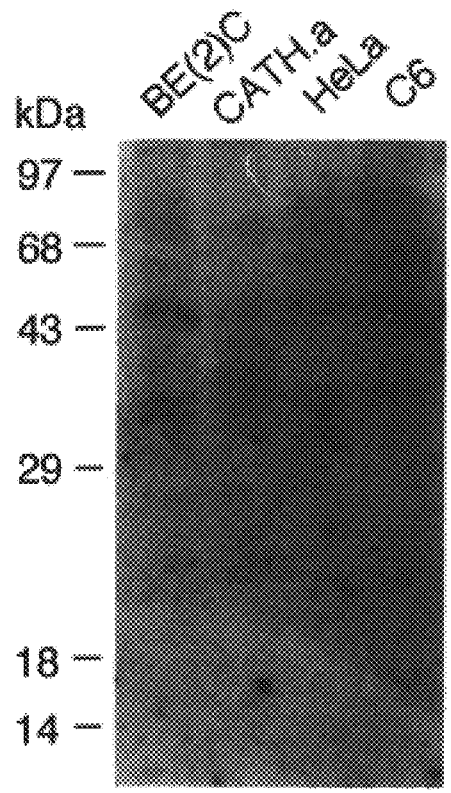

We determined, using DNase I footprint analysis, that domain II selectively interacts with nuclear proteins from noradrenergic cells (FIG. 2). In support of this finding, nuclear extracts from DBH-positive cells robustly formed the complex CII (FIG. 3A). In competition assays, molar excesses of cold domain II oligonucleotide, but not its mutant form or unrelated Sp1 oligonucleotide, abolished formation of CII, strongly suggesting that it represents a sequence-specific complex (FIG. 3B). To further test whether the cognate protein factors of domain II exist in a noradrenergic-specific manner, Southwestern analysis was performed using nuclear proteins prepared from DBH-positive and -negative cells (FIG. 4). This analysis demonstrated that, in DBH-positive cells, several nuclear protein factors interact with domain II. Two protein bands of 39 and 40 kDa were detected in SK-N-BE(2)C cells, while protein bands of 38 and 35 kDa were evident in CATH.a cells (FIG. 4A). In contrast, nuclear proteins from DBH-negative cells did not show any prominent signals. In further support of sequence specific binding between domain II and cognate protein factors, a 100-fold molar excess of cold domain II oligonucleotide abolished most of the signals (FIG. 4B).

EXAMPLE 6

Domain II is a Phox2a-binding Site

Figures 5A, 5B:
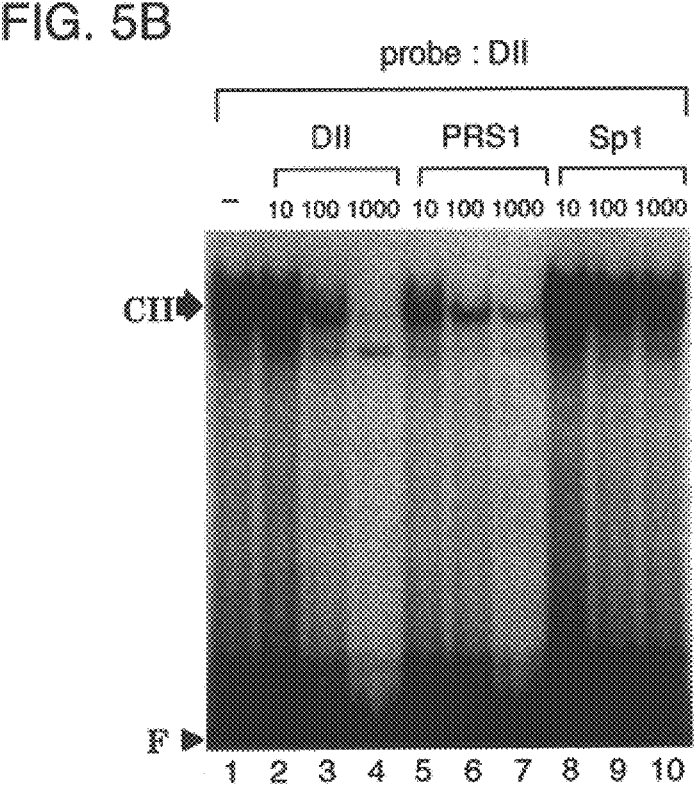
FIG. 5A is a schematic illustration showing nucleotide sequences of the HD binding site of domain IV (referred to herein as PRS1) and wild type and mutant of domain II oligonucleotides. The ATTA motifs are indicated by asterisks. Mutated bases are shown in the mutant oligonucleotides. Dots represent unchanged sequences.
FIG. 5B is a photograph of an autoradiograph showing that the DNA-protein complexes formed with SK-N-BE(2)C nuclear proteins and the DII oligonucleotide were competed by molar excesses of different cold oligonucleotides as indicated above each panel. 30 μg of nuclear proteins were used in each binding reaction.

Our findings that domain II binds to nuclear proteins in a cell-specific manner, and that its mutation is associated with a severe loss of DBH promoter function only in noradrenergic cells, prompted us to characterize and identify the cognate nuclear factors. The nucleotide sequence of domain II is A/T-rich, and our previous sequence search did not reveal significant homology to any known cis-acting motif. To determine nucleotide bases important for domain II-protein factor interaction, we performed EMSA using domain II or mutant oligonucleotides containing double or triple base substitutions at different locations as probes (FIG. 5A). Mutant m1 and m2 probes containing base substitutions at the 5' side of domain II were able to form complexes with an efficiency comparable to that of the wild type domain II oligonucleotide with nuclear proteins prepared from SK-N-BE(2)C (lanes 1–3, FIG. 5D) or CATH.a cells. In contrast, m3 and m4 probes no longer generated signals as prominent as the wild type sequence (lanes 4–5, FIG. 5D), indicating that nucleotides residing at the 3' side are critical for domain II-protein interactions. The m4 probe, showing the most severe defect in forming the DNA-protein complex, has base substitutions within the ATTA motif of the HD-binding site at the 3' side, raising the possibility that domain II may represent, in addition to the PRS1 within domain IV, a second Phox2a/Phox2b-binding site. To test this, we further analyzed DNA-protein interaction at domain II using competition and supershift assays. Using the DII oligonucleotide as the probe, the cold PRS1 oligonucleotide was able to compete formation of DNA-protein complexes even more efficiently than the cold DII oligonucleotide (lanes 1 to 10, FIG. 5B). These competition assays indicate that common nuclear factors interact with domain IV and, with a lower affinity, with domain II. The lower affinity exhibited by domain II is presumably due to the fact that PRS1 contains two ATTA core motifs, while domain II has only one such motif.

Figures 1, 5C:
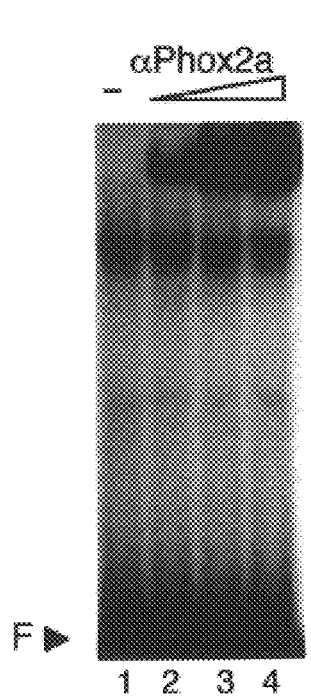
FIG. 5C is a series of photographs of autoradiographs showing antibody supershift assays that indicate that Phox2a binds to both domain II (SEQ ID NO: 2) and PRS1(SEQ ID NO: 1). Coincubation of nuclear proteins with increasing amounts of 1 μl of $10^{-2}$ (lanes 2 and 6), $10^{-1}$ (lanes 3 and 7) and 1:3 dilutio 4 and 8) of Phox2a-specific antibody resulted in the generation of a supershifted band (indicated by an arrowhead) in a dose-responsive manner with both PRS1 (left panel) and DII oligonucleotide (right panel). Coincubation with either SP1 or AP2-specific antibody (0.1 μg each) neither generated the supershifted band nor diminished formation of CII (lanes 9 and 10).
Figures 2, 5C:
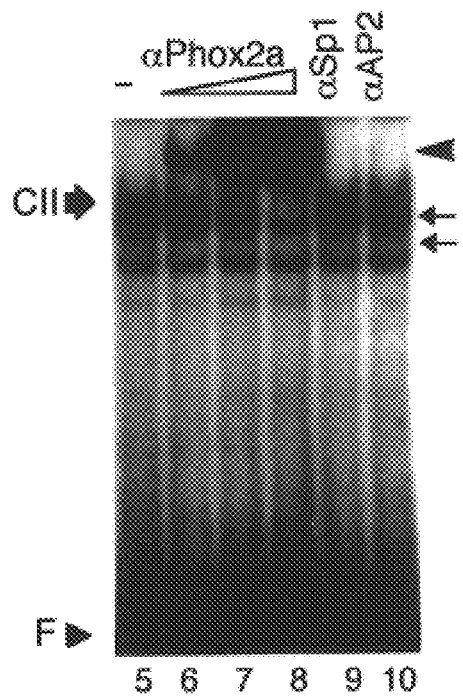

To address whether domain II-protein complexes contain Phox2a, a supershift assay was performed using Phox2a-specific antibody. In a control experiment using radiolabelded PRS1 oligonucleotide as the probe, coincubation with Phox2a-specific antibody generated a supershifted band in a dose-response manner (FIG. 5C; lanes 1 to 4). When the radiolabeled domain II oligonucleotide was used as the probe, coincubation of SK-N-BE(2)C nuclear extracts with Phox2a-specific antibody diminished formation of CII and generated a supershifted band in a dose-dependent manner (FIG. 5C; lanes 6 to 9). In contrast, coincubation with specific antibodies against Sp1 (FIG. 5C; lane 9) or AP2 (FIG. 5C; lane 10) neither diminished CII nor generated a supershifted band. Coincubation of Phox2a-specific antibody with nuclear proteins from CATH.a or PC12 cells similarly resulted in generation of a robust supershifted band. In contrast, coincubation with preimmune serum or nuclear extracts from C6 or HeLa cells did not produce any detectable signal of supershifted band using either radiolabeled PRS1 or domain II oligonucleotide. Taken together, these data indicate that Phox2a is directly involved in formation of CII.

Figures 1, 5D:
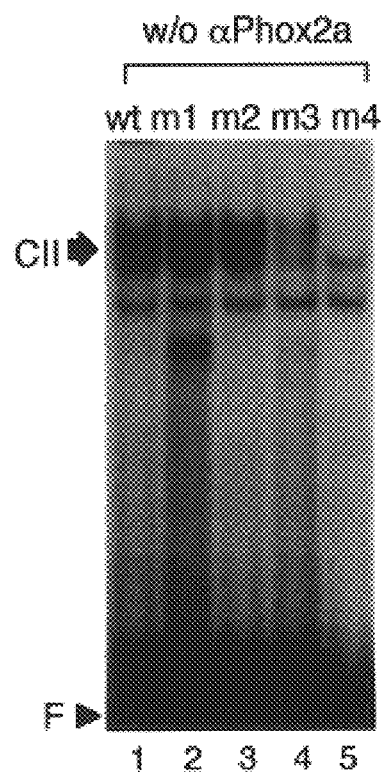
FIG. 5D is a series of photographs of autoradiographs showing the determination of nucleotide bases important for domain II-protein interaction in the absence (left panel) or presence (right panel) of Phox2a-specific antibody. The supershifted complex is indicated by an arrowhead. Two nonspecific bands are indicated by arrows.
Figures 2, 5D:
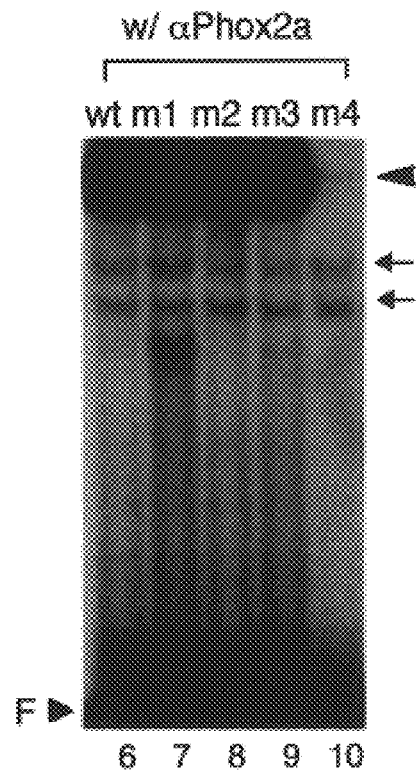

The signals of the supershifted band were significantly stronger than those of original DNA-protein complexes using either PRS1 or domain II probe. In the supershift assay using wild type and mutant domain II oligonucleotides, all probes except m4 formed a robust supershifted band, strongly suggesting that the ATTA motif is the only subregion that is essential for interaction of domain II with Phox2a (FIG. 5D). Similar results were obtained using lower amounts of antibodies. Although the m3 mutant did not itself form intact amounts of DNA-protein complexes, it was able to generate a supershifted band with a comparable signal (FIG. 5D; compare lanes 4 and 9 with 1 and 6). One interpretation for this finding is that m3 has comparable affinity to Phox2a but does not bind to other binding proteins as efficiently as the wild type domain II. Alternatively, association of Phox2a with the specific antibody may have overcome its low affinity to m3 sequence.

EXAMPLE 7

Figure 6A:
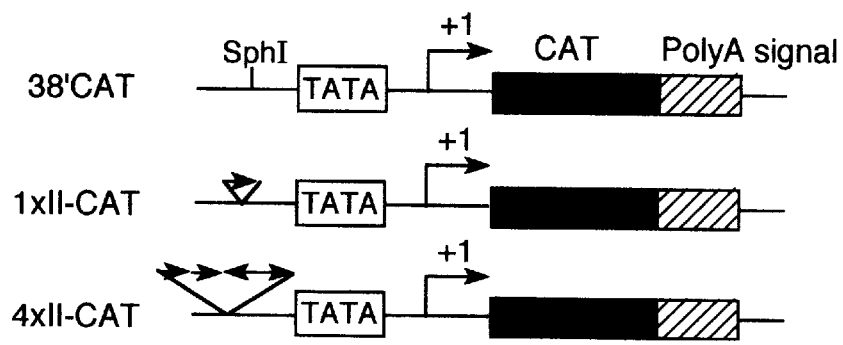
FIG. 6A is a diagram of reporter plasmids. 38' CAT is a minimal DBH-CAT reporter plasmid that contains the TATA box and the transcription start site of the human DBH gene. A single copy of domain II oligonucleotide is cloned at the SphI site upstream of the TATA box, resulting in 1xII-CAT. Likewise, four tandem copies of domain II oligonucleotide are cloned at the SphI site. Sequence analysis of 4xII-CAT showed that, among the four copies of domain II, the third copy was in opposite orientation as indicated by the direction of arrows.
Figure 6B:
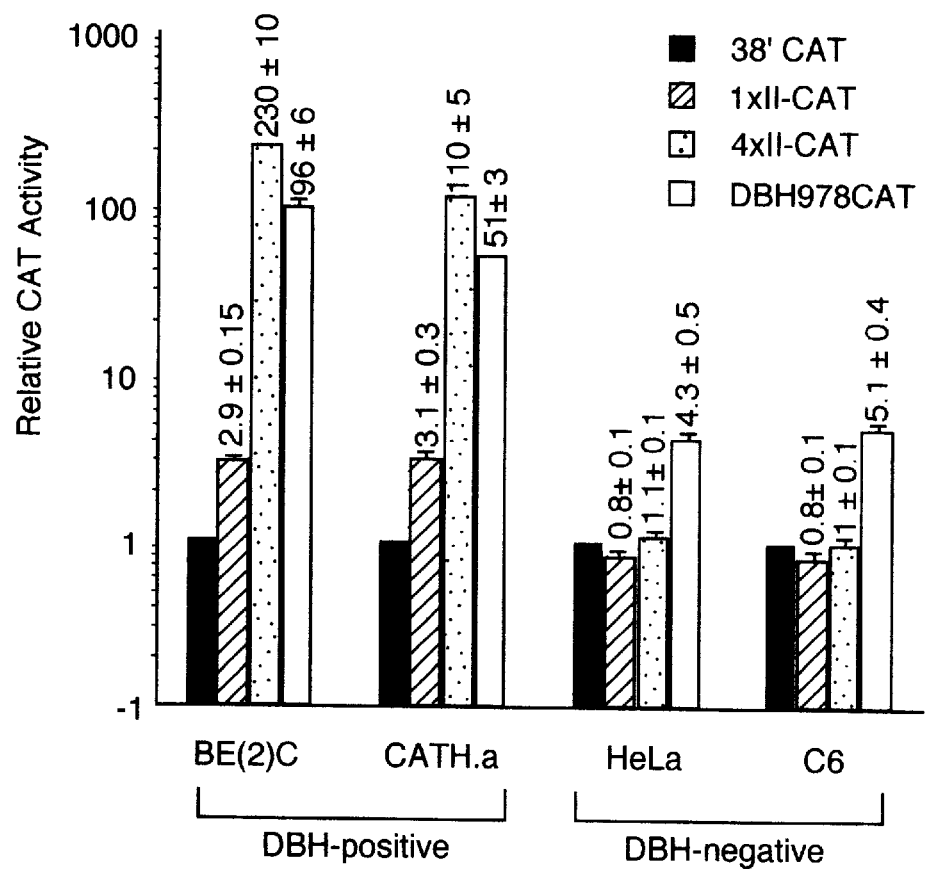
FIG. 6B is a schematic illustration showing that domain II sequence motifs can activate the promoter activity in a noradrenergic-specific manner. The CAT activity driven by each construct is presented relative to that of 38' CAT, with mean±SEM for six to eight determinations plotted on a logarithmic scale. This experiment was repeated once more in triplicate, using plasmid DNAs independently prepared, and resulted in similar patterns.
Figure 6C:
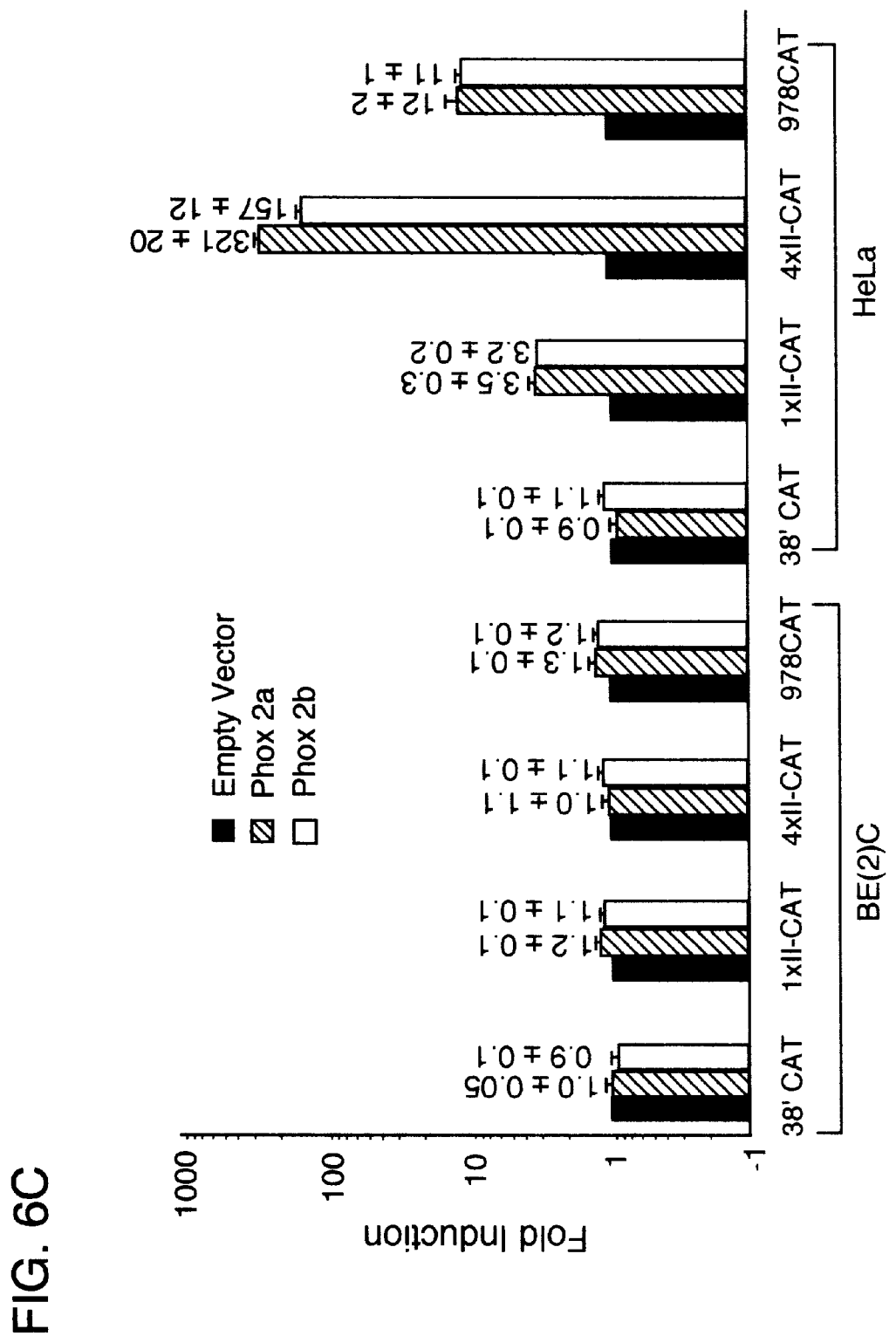
FIG. 6C is a schematic illustration showing that domain II can mediate transactivation by Phox2a and Phox2b. HeLa and SK-N-BE(2)C cells were transiently cotransfected with reporter plasmids and pRC/Phox2a or pRC/Phox2b with a molar ratio of 0.5. The CAT activity driven by each reporter construct itself was set to 1.0 to compare transactivation by Phox2a or Phox2b. Fold induction by Phox2a/Phox2b cotransfection is presented as mean±SEM values from six to eight samples on a logarithmic scale.

Domain II Upregulates the DBH Minimal Promoter Activity in a Noradrenergic-specific Manner and Mediates Phox2a/Phox2b-induced Transcriptional Activation A single copy of domain II was subcloned in the correct orientation in front of the minimal promoter region of the DBH gene containing the TATA box and transcription start site (1xII-CAT; FIG. 6A), and its transcriptional activity was examined by transient transfection assays in DBH-positive and -negative cell lines. As shown in FIG. 6B, 1xII-CAT drives expression of the reporter gene 3-fold higher than that driven by 38' CAT in DBH-expressing SK-N-BE(2)C and CATA.a cells, but not in DBH-negative HeLa and C6 cells. Furthermore, cotransfection assay shows that Phox2a or Phox2b activates the reporter gene expression driven by 1xII-CAT plasmid 3- to 4-fold in DBH-negative HeLa (FIG. 6C) and C6 cells. In DBH-expressing cell lines, in contrast, cotransfection of Phox2a or Phox2b activated the promoter activity of 1xII-CAT construct only marginally, if at all (FIG. 6C). These data confirm that domain II is a noradrenergic-specific enhancer that mediates Phox2a-responsive transcriptional activation. The promoter activity of a single copy of domain II by itself, however, represented only 5% of the intact DBH promoter activity in the DBH-positive cell lines (FIG. 6B). To address whether multiple copies of domain II could synergistically activate the DBH minimal promoter activity in a cell-specific manner, we subcloned four tandem copies of domain II using the same 38° CAT plasmid (FIG. 6A). The resulting plasmid, 4xII-CAT plasmid, increased the DBH minimal promoter activity by 100- to 200-fold in DBH-positive cell lines. Thus, four tandem copies of domain II exhibited at least 2-fold of the promoter activity of the intact DBH promoter-enhancer region in our transient transfection assay. Strikingly, in DBH-negative cell lines the CAT activity driven by 4xII-CAT plasmid was comparable to that of 38' CAT, demonstrating a tight cell specificity. Furthermore, cotransfection with Phox2a/Phox2b-expression plasmid increased CAT activity by 200- to 300-fold only in DBH-negative cell lines. These results suggest that multiple copies of domain II, domain IV, or a combination thereof, may be used for targeted transgene expression to noradrenergic neurons. Additionally, the multimerization of any enhancer domain that binds Phox2a or Phox2b would likely result in robust, noradrenergic cell-specific expression.

Figure 6D:
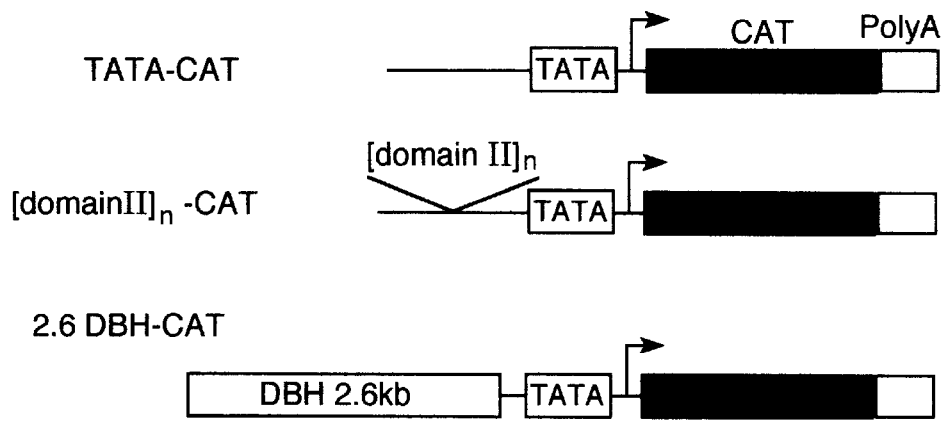
FIG. 6D is a diagram of reporter plasmids. TATA-CAT is a minimal DBH-CAT reporter plasmid that contains the TATA box and thr transcription start site of the human DBH gene. DBH2.6 kb-CAT contains the 2.6 kb promoter sequence of the human DBH gene. [domain II]n-CAT contains domain II sequence at a copy number of n, operably linked to the minimal DBH promoter.
Figure 6E:
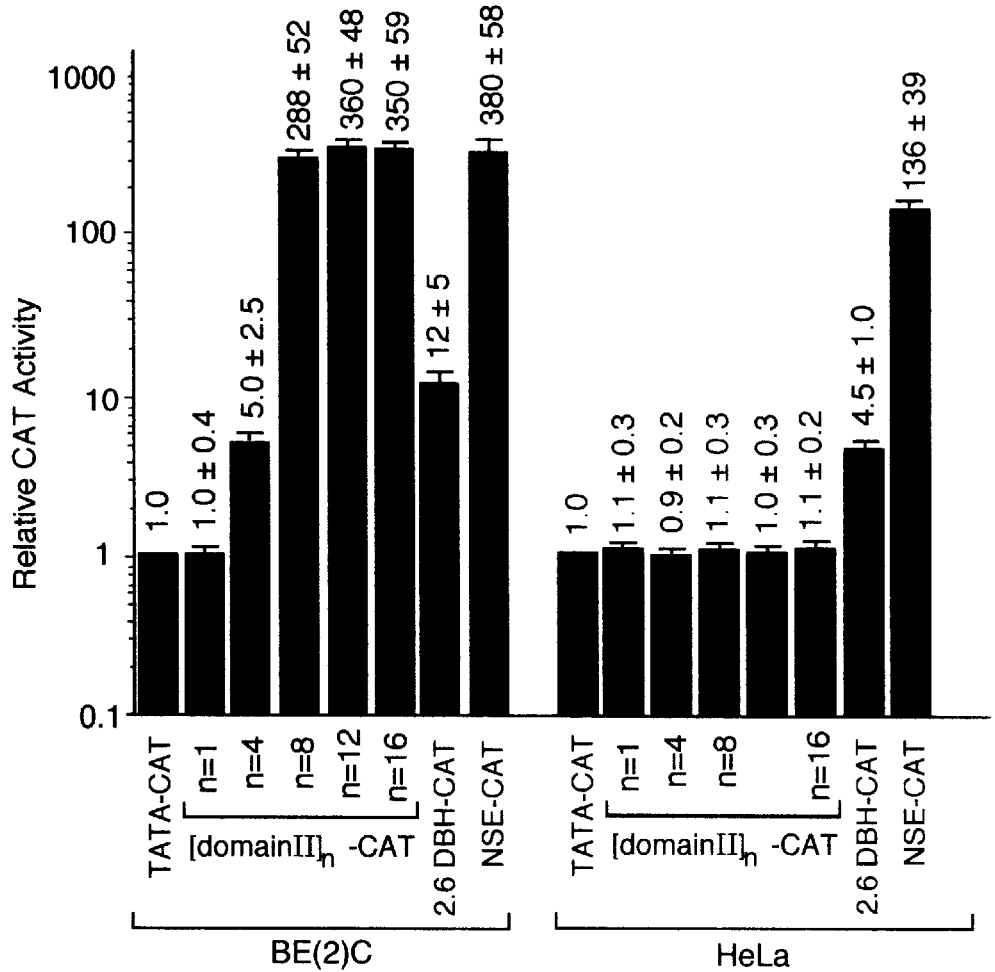
FIG. 6E shows the results of transient transfection assays of the reporter plasmids shown in FIG. 6D into DBH-positive BE(2)C cells and DBH-negative HeLa cells. The normalized CAT activity from each construct is presented relative to TATA-CAT, with mean±SEM for six to eight determinations.

In the foregoing example, the four copies of domain II were continuous (i.e., there was no linker sequence between each domain II). We repeated the experiments using between 1 and 16 copies of domain II, but this time the domains were separated by the linker sequence 5'-AGATCC-3' (SEQ ID NO: 5). As shown in Table 1, 16 copies of domain II, operably linked to a promoter from the human DBH gene, increased promoter activity 2000-fold, and greater than 20-fold the promoter activity exhibited by DBH978CAT. A similar result was also acheived with multimerized domain II in which there was no spacer sequence (Fig; in this example, the maximal increase was about 350-fold with 16 copies (FIGS. 6D and 6E).

TABLE 1

| Number of copies of domain II | Noradrenergic cell lines | Nonneuronal cell lines |
|---|---|---|
| 1 | 1 | 1 |
| 4 | 12 | 1 |
| 8 | 1000 | 1 |
| 12 | 2000 | 1 |
| 16 | 2000 | 1 |

EXAMPLE 8

Multimerized DBH Enhancers Confer Robust and Cell-specific Expression in Vivo

Figure 7A:
FIG. 7A is a diagram of recombinant adenoviral vectors. A green fluorescent protein (GFP) gene under the CMV promoter was incorporated into all backbones to allow for direct observation of the location and efficiency of infection in brain.
Figure 7A:
Figure 7A:
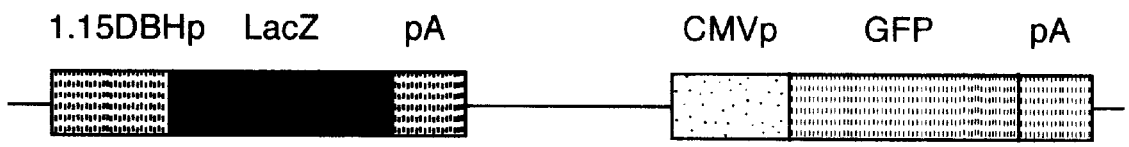
Figures 1, 7B:
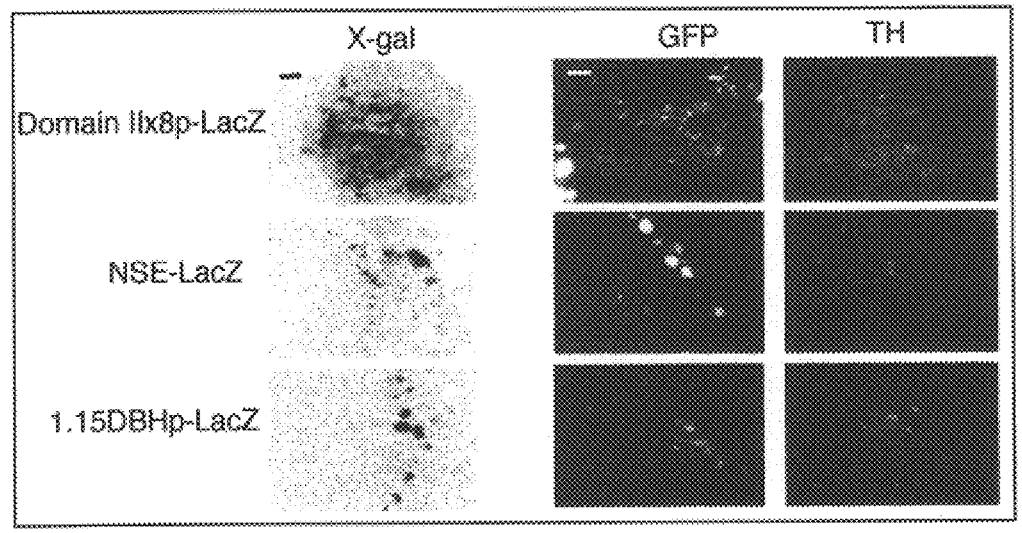
FIG. 7B is a series of photographs showing expression of lacZ following infection with the adenoviral vectors of FIG. 7A. Adenoviruses were unilaterally injected into the locus caeruleus, cerebellum, and dentate gyrus. β-galactosidase expression after four days was examined by X-gal staining. GFP expression was examined to confirm the delivery of viruses to the targeted area.
Figures 2, 7B:
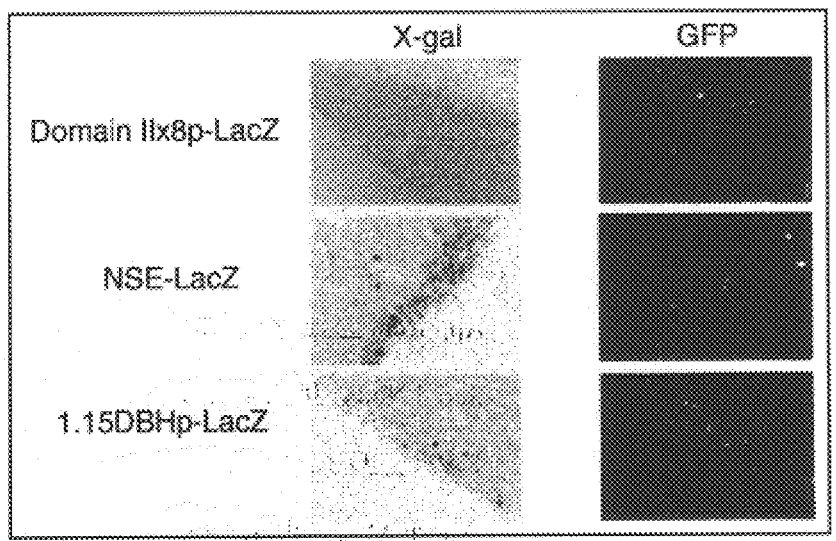
Figures 3, 7B:
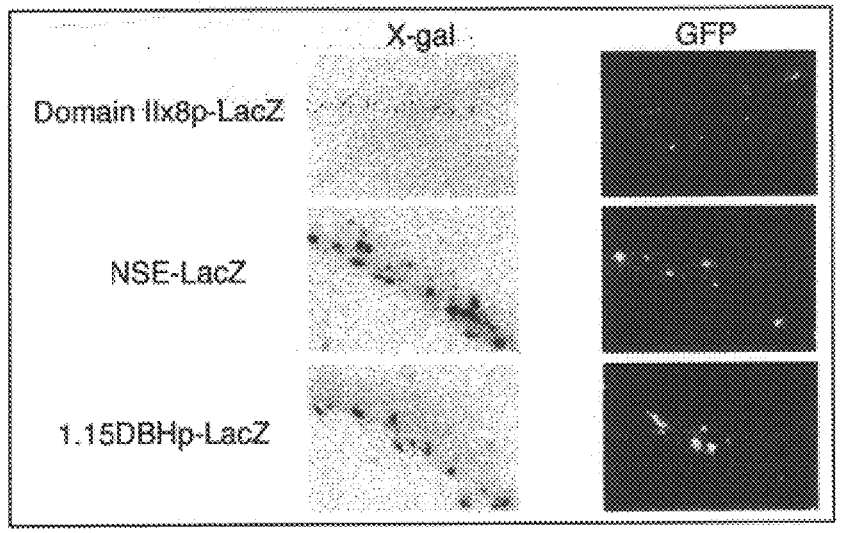

We constructed an adenoviral vector in which eight copies of domain II were operably linked to the minimal DBH promoter and the lacZ gene (FIG. 7A). This vector (or a control vector) was then stereotactically injected into the locus caeruleus, cerebellum, or dentate gyrus. Four days later, the expression of the lacZ reporter gene was determined by X-gal staining. The animals injected with the adenoviral vector containing the multimerized domain II had showed robust expression in regions in which noradrenergic cells are found, an no expression elsewhere (FIG. 7B). From these data, we conclude that infection with expression vectors containing multimerized DBH enhancer domains results in strong expression (i.e., greater than that achieved with the 2.6 kb DBH proximal sequence) in noradrenergic cells and very little or no expression elsewhere. This noradrenergic cell-specific was not observed with the vector containing the 2.6 kb DBH proximal sequence (FIG. 7B).

Example 9

Identification of a Phox2a Binding Site

DNAse I footprinting analysis revealed a Phox2A binding site at −105 to −85 of the DBH proximal region (5'-GAGGGAAAATTGGATTCCCCG-3'; SEQ ID NO: 6). We performed a mutagenesis analysis of this site. Two mutant constructs were made. We predicted that the first (5'-GAGGGAAAGCCTTCGGC CCCG-3' (SEQ ID NO: 7); mPBD3) would abolish Phox2A binding, and the second (5'-GAGGGAAAATTGGATTACCCG-3' (SEQ ID NO: 8); mPBD3(ATTA)) would improve binding. Each of these predictions was realized (Table 2).

TABLE 2

|  | BE | M17 | HeLa | C6 | HepG2 |
|---|---|---|---|---|---|
| wt | 2.4 | 3.2 | 0.1 | 0.2 | 0.04 |
| mPBD3 | 0.12 | 0.32 | 0.08 | 0.14 | 0.027 |
| mPBD3(ATTA) | 28.8 | 21.1 | 0.11 | nd | 0.04 |

EXAMPLE 10

Optimization of Phox2a Binding Sites

Based on our findings, it is likely that the endogenous Phox2a binding sites are not optimized. Optimization can be performed using the methods described herein. In one example, domain II is systematically altered and tested for expression levels and cell specificity. Optimized enhancer domains are useful as multimerized enhancer domains, as is described throughout the specification. They are also useful in the intact promoter. For example, it may be desirable to use the 1.1 kb or 2.6 kb proximal region for the production of a transgenic animal (e.g., a transgenic mouse) for the purposes of, for example, drug screening. In this context, one or more Phox2a binding sites can be altered to optimize or improve Phox2a binding or Phox2a-mediated transcription. Preferably, the binding or transcription is improved at least two-fold.

The foregoing results were obtained with the following methods.

Cell Culture and Transient Transfection Assays

Human neuroblastoma SK-N-BE(2)C and SK-N-BE(2) M17 and mouse central noradrenergic neuron-derived CATH.a cell lines were maintained as described (Kim et al., J. Neurosci., 14:7200–7207, 1994; Ishiguro, supra; Suri et al., J. Neurosci. 13:1280–1291, 1993) and used as the DBH-positive system. The HeLa and rat C6 glioma cell lines were grown in Dulbecco's modified Eagle's medium supplemented with 10% fetal calf serum, streptomycin, and penicillin and used as the DBH-negative system in this study.

Transfection was performed by the calcium phosphate coprecipitation method as previously described (Ishiguro, supra; Seo et al., J. Neurosci., 16:4102–4112, 1996). For the SK-N-BE(2)C and SK-N-BE(2)M17 cell lines, each 60-mm dish was transfected with 2 mg of the reporter construct, 1 mg of pRSV-βgal, varying amounts of the effector plasmid, and pUC 19 plasmid to a total of 5 mg DNA. For the other cell lines, twice as much DNA was used in transfection. Plasmids used for transient transfection assays were prepared using Qiagen columns (QIAGEN Inc., Santa Clarita, Calif.). To correct for differences in transfection efficiencies among different DNA precipitates, CAT activity was normalized to that of β-galactosidase. CAT and β-galactosidase activities were assayed as previously described (Ishiguro, supra; Seo, supra).

DNA Constructions

The DBH978CAT and DBH262CAT reporter constructs contain the 978 bp and 262 bp upstream sequences of the human DBH gene, respectively, fused to the bacterial CAT gene (Ishiguro, supra). A series of human DBH promoter-CAT reporter constructs with progressive deletions of proximal protein-binding sites were generated using pBLCAT3-1, which drives significantly lower background CAT activity compared to pBLCAT3 (Luckow and Schutz, Nucl. Acids. Res., 15:5490, 1987). 262' CAT construct was generated by ligating the 271 bp SphI-XbaI fragment of 262CAT plasmid with the 4.3 kb SphI-XbaI backbone of pBLCAT3-1 plasmid. 114' CAT construct was made by ligating the 726 bp HindIII-NcoI fragment with HindIII-NcoI backbone of pBLCAT3-1 plasmid. To generate 142' CAT and 62' CAT plasmids, polymerase chain reaction was performed using oligonucleotides 5'-GACATGCATGCGCAGGCTGAGTGCTTGGC-3' (SEQ ID NO: 9) and 5'-CATTTTAGCTTCCTTAGC-3' (SEQ ID NO: 10), and 5'-GACATGCATGCGCTGCCTGGACCCACCCC-3' (SEQ ID NO: 11) and 5'-CATTTTAGCTTCCTTAGC-3' (SEQ ID NO: 12), respectively, using DBH978CAT as the template. The 163 bp and 71 bp fragments were isolated after digesting the PCR products with SphI and XbaI, and then subcloned into pBLCAT3-1 that had been digested with SphI and XbaI, resulting in 142' CAT and 62' CAT plasmids, respectively. 38° CAT plasmid was constructed as follows: polymerase chain reaction was performed using oligonucleotides 5'-GACATGCATGCGTCCAGGGCATAAATGGC-3' (SEQ ID NO: 13) and 5'-CATTTTAGCTTCCTTAGC (SEQ ID NO: 14) and DBH978CAT plasmid as the template. A 70 bp fragment was isolated after digesting the PCR product with SphI and XhoI and subcloned to pBLCAT3-1 that had been digested with SphI and XhoI. pBLCAT3-1 is a derivative of pBLCAT3 and was constructed by deleting the CRE-like sequence and TATA-like sequence upstream of multiple cloning sites. The resultant plasmid 38' CAT, containing the TATA box and transcription start site of the human DBH gene fused to the CAT gene, was isolated and confirmed by sequence analysis. upstream sequences and junction regions of these deletional constructs were confirmed by sequencing analysis.

Base substitutions were generated in the context of the 978 bp upstream sequence using the QuickChange™ PCR-based site-directed mutagenesis kit (Stratagene, La Holla, Calif.) according to the manufacturer's procedure. The following oligonucleotides were used in the mutagenesis procedure using DBH978CAT plasmid as the template: 5'-CCTGGACCCACTATGTTCAGGACCAG-3' (SEQ ID NO: 15) and 5'-CCTGGTCCTGAACATAGTGGGTCCAG-3' (SEQ ID NO: 16) for domain I mutant, 5'-CCGCTAGACAAGCAGACGTACCCGTGCTG-3' (SEQ ID NO: 17) and 5'-GCAGCACGGGTACGTCTGCTTGTCTAGCG-3' (SEQ ID NO: 18) for domain II mutant, and 5'-TGAGTGCTTGGCCTGGTTAGCAAGCTTGTGG GAGG-3' (SEQ ID NO: 19) and 5'-CCCTCCCACAAGCTTGCTAACCAGGCCA AGCACTC-3' (SEQ ID NO: 20) for domain III mutant. For domain IV, the following primers were used: 5'-CCATGTGTCACCGGTGCCAATTAG-3' (SEQ ID NO: 21) and 5'-CTAATTGGCACCGGTGACACATGG-3' (SEQ ID NO: 22) for mHD1, 5'-CATTAGTGCCAACCGGAGGAGGGC-3' (SEQ ID NO: 23) and 5'-GCCCTCCTCCGGTTGGCACTAATG-3' (SEQ ID NO: 24) for mHD2. 5'-CACCGGTGCCAACCGGAGGAGGGCAG'3' (SEQ ID NO: 25) and 5'-GCTGCCCTCCTCCGGTTGGCACCGGT-3' (SEQ ID NO: 26) were used to produce mHD1+2 using mHD1 as the template. In each case, the first set of primers represents coding strand sequences containing the desired mutations, and the second set of primers represents the corresponding noncoding strand sequences. Constructs with correct mutations were screened by restriction enzyme digestion and sequencing analysis.

A single copy of the domain II oligonucleotide (see below) was subcloned to the SphI site of 38' CAT plasmid. After restriction and sequencing analyses, the 1xII-CAT construct containing a single copy of domain II in correct orientation was selected. In addition, the same domain II oligonucleotide was ligated after Klenow reaction. A DNA fragment of 92 bp was isolated and subcloned to the same SphI site of 38' CAT plasmid. 4xII-CAT plasmid, which contains four copies of domain II (three copies in the right orientation and one in the opposite orientation; FIG. 6), was isolated and confirmed by sequence analysis. Recombinant constructs that can express Phox2a or Phox2b were used as effector plasmids. pRc/Phox2a containing the full length cDNA for Phox2a under the control of the CMV promoter has been described previously (Valarche, supra). A full-length cDNA fragment encoding Phox2b was isolated by digesting pBluescript KS II+/Phox2b (Pattyn et al., Development, 125: 599–608, 1997) with HindIII and ApaI, and was subcloned downstream of the CMV promoter using the same pRC/CMV vector, resulting in pRC/Phox2b.

Preparation of Nuclear Extracts, EMSA, and DNase I Footprinting

Nuclear extracts were prepared from different cell lines according to the procedure described by (Dignam et al., Nucl. Acid Res., 11:1475–1489, 1983). Sense and antisense oligonucleotides corresponding to the sequences of domains I, II, and III were synthesized, and the sense and antisense oligonucleotides were annealed, gel-purified, and $^{32}$P-labeled by T4 DNA kinase and used as probes in electrophoretic mobility shift assays (EMSA). EMSA and antibody coincubation experiments were performed using 30,000 to 50,000 cpm of labeled probe (approximately 0.05 to 0.1 ng) and nuclear extracts (10 to 30 mg) in a final volume of 20 ml of 12.5% glycerol, 12.5 mM HEPES (pH 7.9), 4 mM Tris-HCl (pH 7.9), 60 mM KCl, 1 mM EDTA, and 1 mM DTT with 1 mg of poly(dI-dC). Competition binding assays were performed by adding nonradioactive competitor oligonucleotides in a molar excess prior to adding $^{32}$P-labeled oligonucleotides. For supershift assay, antibody was coincubated with the nuclear extract mix for 30 min at room temperature prior to adding the radiolabeled probe. Antibodies against Sp1, Sp3, Sp4, and AP2 were purchased from Santa Cruz Biotechnology, Inc. (Santa Cruz, Calif.). A Phox2a-specific antibody (#60) raised against a polypeptide (Y75 to R88) residing immediately upstream of the HD was used in the supershift assay. Recombinant AP2 proteins were purchased from Promega Corporation (Madison, Wis.) and used for EMSA with $^{32}$P-labeled DIII oligonucleotide and consensus AP2 sequence as probes. DNase I footprinting assay was performed using the wild type and mutant human DBH 5' proximal fragments that had been prepared by polymerase chain reaction as the probe as described (Seo, supra). After incubating approximately 30,000 cpm of labeled probe with 150–200 mg of nuclear extracts from different cell lines, freshly diluted DNase 1 (1.5 to 2.5 units) was added to a final volume of 40 ml and incubated for 90 seconds at the room temperature. The precise amount of DNase I was empirically determined for each extract to ensure an even pattern of digested bands. For the sample without nuclear extracts, much lower amounts of DNase I (approximately one tenth) were used. The probe DNA treated with DNase I was purified and an aliquot (approximately 10 to 20%) of each sample was analyzed on a 6% polyacrylamide/8M urea-sequencing gel followed by autoradiography with an intensifying screen. Location of the protected area was determined by Maxam-Gilbert sequencing of labeled probes.

Southwestern Blot Analysis

Southwestern blotting was performed as described (Michael et al., Science 239: 1531–1533, 1988). Two sets of nuclear proteins prepared from different cell lines (100 mg each per lane) were mixed with 10 ml of 2× sample loading buffer (4% SDS, 14% glycerol, 0.16 M Tris, pH 6.8, 0.1% BPB, 5 mM DTT) and buffer D (Dignam, supra) to a final volume of 20 ml, heated to 95° C. for 5 min and then separated on a denaturing SDS-10% polyacrylamide gel. The protein bands were transferred to a nitrocellulose membrane, and the nonspecific protein bands on the membrane were blocked by three washes of 45 min in 10 mM Tris, pH 7.5, 5% nonfat dry skim milk, 10% glycerol, 2.5% Nonindet P40, 0.1 mM DTT, and 150 mM NaCl at 25° C. The membrane was then rinsed briefly in binding buffer (10 mM Tris, pH 7.5, 40 mM NaCl, 1 mM EDTA, 1 mM DTT, 8% glycerol, 0.125% nonfat dry skim milk) and was incubated in 10 ml of binding buffer containing 500,000 cpm/ml end-labeled domain II oligonucleotide probe and 10 mg/ml poly(dI-dC). After incubation overnight at room temperature, the membranes were removed from the bag, washed with 10 ml of 10 mM Tris, pH 7.5, and 50 mM NaCl three times. The specific protein-domain II interactions were visualized by autoradiography. The specificity of these interactions was determined by adding a 100-fold molar excess of unlabeled domain II oligonucleotide to the second set of separate hybridization bag.

What is claimed is:

1. An enhancer cassette comprising the formula $[X-Y]_n$, wherein each X is, independently, a noradrenergic cell-specific enhancer having 70% sequence identity to SEQ ID NO: 1 or SEQ ID NO: 2 and being capable of binding to Phox2a or Phox2b; each Y is, independently, absent or is a mononucleotide or polynucleotide that contains between one and thirty nucleotides; and n is an integer between five and thirty, inclusive.

2. The enhancer cassette of claim 1, wherein Y is absent or is a mononucleotide or polynucleotide that contains between one and six nucleotides.

3. The enhancer cassette of claim 1, further comprising an RNA polymerase binding site and a transcription initiation site.

4. The enhancer cassette of claim 1, wherein n is greater than eight.

5. The enhancer cassette of claim 4, wherein n is ten or greater.

6. The enhancer cassette of claim 1, wherein n is an integer between five and twenty, inclusive.

7. An expression vector comprising an enhancer cassette having the formula $[X-Y]_n$, wherein each X, independently, is a noradrenergic cell-specific enhancer having 70% sequence identity to SEQ ID NO: 1 or SEQ ID NO: 2 and being capable of binding to Phox2a or Phox2b; each Y is, independently, absent or is a mononucleotide or polynucleotide that contains between one and thirty nucleotides; and n is an integer between five and thirty, inclusive.

8. The expression vector of claim 7, wherein n is greater than eight.

9. The expression vector of claim 8, wherein n is ten or greater.

10. The expression vector of claim 7, wherein each Y is, independently, absent or is a mononucleotide or polynucleotide that contains between one and six nucleotides, inclusive.

11. The expression vector of claim 7, wherein n is an integer between five and twenty, inclusive.

12. A method of expressing a nucleic acid molecule in a noradrenergic cell, comprising expressing in said noradrenergic cell and expression vector comprising an enhancer cassette having the $[X-Y]_n$ operably linked to said nucleic acid molecule, wherein each X, independently, is a noradrenegic cell-specific enhancer having 70% sequence identity to SEQ ID NO: 1 or a SEQ ID NO: 2 and being capable of binding to a Phox2a or Phox2b; each Y is, independently, absent or is a mononucleotide or polynucleotide that contains between one and thirty nucleotides; and n is an integer between five and thirty, inclusive.

13. The method of claim 12, wherein each X, is independently selected from the group consisting of SEQ ID NO: 1 and SEQ ID NO: 2.

14. The method of claim 12, wherein n is greater than eight.

15. The method of claim 14, wherein n is ten or greater.

16. The method of claim 12, wherein each Y is, independently, absent or is a mononucleotide or polynucleotide that contains between one and six nucleotides, inclusive.

17. The method of claim 12, wherein n is an integer between five and twenty, inclusive.

18. An enhancer cassette comprising the formula $[X-Y]_n$, wherein each X, independently, is a nucleic acid molecule selected from SEQ ID NO: 1 and SEQ ID NO:2; each Y, independently, is a nucleic acid molecule containing between zero and thirty nucleotides; and n is an integer between five and thirty, inclusive.

19. The enhancer cassette of claim 18, wherein n is greater than eight.

20. The enhancer cassette of claim 19, wherein n is ten or greater.

21. The enhancer cassette of claim 18, wherein n is an integer between five and twenty, inclusive.

* * * * *